(12) United States Patent
Reilly et al.

(10) Patent No.: US 10,107,820 B2
(45) Date of Patent: Oct. 23, 2018

(54) METHOD OF IDENTIFYING PEPTIDES

(75) Inventors: James P. Reilly, Bloomington, IN (US); Liangyi Zhang, South San Francisco, CA (US)

(73) Assignee: The Trustees of Indiana University, Indianapolis, IN (US)

( * ) Notice: Subject to any disclaimer, the term of this patent is extended or adjusted under 35 U.S.C. 154(b) by 67 days.

(21) Appl. No.: 13/519,255

(22) PCT Filed: Dec. 31, 2010

(86) PCT No.: PCT/US2010/062632
§ 371 (c)(1),
(2), (4) Date: Jun. 26, 2012

(87) PCT Pub. No.: WO2011/082376
PCT Pub. Date: Jul. 7, 2011

(65) Prior Publication Data
US 2012/0282641 A1    Nov. 8, 2012

Related U.S. Application Data

(60) Provisional application No. 61/291,442, filed on Dec. 31, 2009.

(51) Int. Cl.
*G01N 27/62* (2006.01)
*G01N 33/68* (2006.01)
*G06F 19/18* (2011.01)
*G06F 19/24* (2011.01)

(52) U.S. Cl.
CPC ..... *G01N 33/6818* (2013.01); *G01N 33/6848* (2013.01); *G06F 19/18* (2013.01); *G06F 19/24* (2013.01)

(58) Field of Classification Search
CPC ............ G01N 33/6818; G01N 33/6848; G06F 19/18; G06F 19/24
See application file for complete search history.

(56) References Cited

U.S. PATENT DOCUMENTS

| | | | |
|---|---|---|---|
| 6,717,130 B2 * | 4/2004 | Bateman | H01J 49/0045 250/281 |
| 6,829,539 B2 * | 12/2004 | Goodlett et al. | 702/20 |
| 2006/0094121 A1 * | 5/2006 | Reid et al. | 436/86 |
| 2008/0070314 A1 * | 3/2008 | Geromanos | G01N 33/6848 436/86 |
| 2008/0272292 A1 * | 11/2008 | Geromanos | G01N 30/7233 250/288 |

OTHER PUBLICATIONS

Thompson et al. (2004) Agnew Chem Int Ed vol. 43 pp. 4791-4794.*
Baldwin et al. (2001) Matrix-Assisted Laser Desorption/Ionization Coupled with Quadrupole/Orthogonal Acceleration Time-of-Flight Mass Spectrometry for Protein Discovery, Identification, and Structural Analysis. Anal. chem. 73: 1707-1720.*
Horn et al. (2000) Proc. Natl. Acad. Sci. 97(19): 10313-10317.*
Zhang et al. (2010) J. Proteome Research 9:3025-3034.*
Zhang et al. (2009) J. Proteome Research 8: 734-742.*
Cui et al. (2005) J. Am. Soc. Mass Spectrom. 16: 1384-98.*
Morgan et al. (2005) Meth. Enzymol. 402: 186-209.*
Bringans et al. (2008) Rapid commun. Mass Spectrom. 22: 3450-54.*
Thompson, et al. "Fragmentation of Singly Charged Peptide Ions by Photodissociation at Lambda-157nm" Angew Chem Int Ed vol. 43, p. 4791-4794 (2004) p. 4792, left col., para 3, Fig. 2, p. 4793, right col, para 3.
International Search Report and Written Opinion issued in connection with PCT/US2010/062632 and completed by the U.S. Searching Authority on May 25, 2011 (May 25, 2011).
Bern, M.; Goldberg, D. J. Comput. Biol. 2006, 13, 364-378.
Beardsley, R. L.; J. P. Reilly, Anal Chem. 74, 1884 (2002).
Beardsley, R. L.; Sharon, L.A.; Reilly, J. P. Anal. Chem. 2005, 77, 6300-6309.
Beardsley, R. L., J.A. Karty and J.P. Reilly, J. Rapid Commun. Mass Spectrometry, 14, 2147 (2000).
Brancia, F. L.; Montgomery, H.; Tanaka, K.; Kumanshiro, S. Anal. Chem. 2004, 76, 2748-2755.
Bringans, S.; Kendrick, T. S.; Lui, J.; Lipscombe, R. Rapid Commun. Mass Spectrom. 2008, 22, 3450-3454.
Cul W.; Thompson, M. S.; Reilly, J. P. J. Am. Soc. Mass Spectrom. 2005, 16, 1384-1398.
Frank, A.; Pevzner, P. Anal. Chem. 2005, 77, 964-973.
Fischer, B.; Roth, V.; Roos, F.; Grossmann, J.; Baginsky, S.; Widmayer, P.; Gruissem, W.; Buhmann, J. M. Anal. Chem. 2005, 77, 7265-7273.
Harrison, A.G., Mass Spectrom. Rev. 16, 201 (1997).
Huang, Y.; Triscari, J.M.; Tseng, G. C.; Pasa-Tolic, L.; Lipton, M. S.; Smith, R. D.; Wysocki, V. H. Anal. Chem. 2005, 77, 5800-5813.
R. Kaufmann; D. Kirsch; B. Spengler, Int. J. Mass Spectrom. and Ion Proc. 131, 355 (1994).
Kim, S.; Bandeira, N.; Pevzner, P.A. Mol. Cell. Proteomics 2009, 8, 1391-1400.
T. Keough; R. S. Youngquist; M. P. Lacey, Proc. Natl. Acad. Sci. USA 96, 7131 (1999).

(Continued)

*Primary Examiner* — Lisa J Hobbs
(74) *Attorney, Agent, or Firm* — Barnes & Thornburg LLP

(57) ABSTRACT

Methods of identifying polypeptides have been developed using a de novo sequencing technique. Methods use photodissociation and low-energy fragmentation and the spectra of peptide ions obtained therefrom, such as obtained by post-source decay (PSD), have been developed. The methods include photodissociation and the spectra therefrom obtainable from treating ions with predetermined wavelengths of radiation in the vacuum ultraviolet range of the electromagnetic spectrum. The confidence of amino acid assignments based on x-type ions is evaluated by observing complementary y-, v- and w-type ions that provide additional constraints to sequence identification.

17 Claims, 5 Drawing Sheets

Specification includes a Sequence Listing.

(56) References Cited

OTHER PUBLICATIONS

Ma, B.; Zhang, K. Z.; Hendrie, C.; Liang, C. Z.; Li, M.; Doherty-Kirby, A.; Lajoie, G. Rapid Commun. Mass Spectrom. 2003, 17, 2337-2342.
K. F. Medzihradsky et al., Anal. Chem. 72, 552 (2000).
Mo, L. J.; Dutta, D.; Wan, Y. H.; Chen, T. Anal. Chem. 2007, 79, 4870-4878.
Nielsen, M. L.; Savitski, M. M.; Zubarev, R. A. Mol. Cell. Proteomics 2005, 4, 835-845.
Preiss, J. W.; Setlow, R., J. Chem. Phys. 25, 138 (1956).
Peterson, D. L.; Simpson, W. T., J. Am. Chem. Soc. 79, 2375 (1957).
Savitski, M. M.; Nielsen, M. L.; Kjeldsen, F.; Zubarev, R. A. J. Proteome Res. 2005, 4, 2348-2354.
Spengler, B.; Kirsch, D.; Kaufmann, R.;J. Phys. Chem. 96, 9678 (1992).
Taylor, J. A.; Johnson, R. S. Anal. Chem. 2001, 73, 2594-2604.
Zheng, Z. Anal. Chem. 2004, 76, 6374-6383.
Zhang, L.; Reilly, J. P. Anal. Chem. 2009, 81, 7829-7838.

\* cited by examiner

METHOD OF IDENTIFYING PEPTIDES

CROSS REFERENCE TO RELATED APPLICATIONS

This application is a U.S. national counterpart application of international application serial No. PCT/US2010/062632 filed Dec. 31, 2010, which claims priority to U.S. Provisional Patent Application No. 61/291,442 filed Dec. 31, 2009. The entire disclosures of PCT/US2010/062632 and U.S. Ser. No. 61/291,442 are hereby incorporated by reference.

STATEMENT REGARDING FEDERALLY SPONSORED RESEARCH OR DEVELOPMENT

This invention was made with government support under CHE0518234 awarded by the National Science Foundation. The Government has certain rights in the invention.

INCORPORATION BY REFERENCE OF MATERIAL SUBMITTED ELECTRONICALLY

Incorporated by reference in its entirety is a computer-readable sequence listing submitted concurrently herewith and identified as follows: One 6 Kilobyte ASCII (Text) file named 221596_ST25.txt created on Jun. 26, 2012.

TECHNICAL FIELD

This invention relates generally to the analysis of molecules by mass spectrometry and more specifically to the de novo sequencing of peptides and proteins by fragmentation and mass spectrometry.

SUMMARY

According to the present disclosure, a method of identifying peptides, proteins, enzymatic digests of proteins, carbohydrates, glycopeptides, glycoproteins, nucleic acids, synthetic polymers, and the like is described using mass spectrometry (MS). De novo sequencing methods have been developed to derive peptide sequences from tandem mass spectra without reference to a database.

In illustrative embodiments, a method of identifying a peptide comprises obtaining a first set of mass spectral data, obtaining a second set of mass spectral data, and identifying the peptide using a de novo sequencing algorithm. The algorithm exploits similarities and differences between the first set of mass spectral data and the second set of mass spectral data. The similarities arise from the presence of related peaks between the two spectra. In one embodiment, the method includes identifying the peaks associated with high-energy fragments and low-energy fragments. In another embodiment, the peaks associated with the high-energy fragments result from a high-energy fragmentation, such as the high-energy fragmentation of a vacuum ultraviolet photodissociation source. In another embodiment, the low-energy fragments are obtained through a low-energy process, such as post-source decay following matrix assisted laser desorption ionization or collision-induced dissociation following electrospray ionization.

In illustrative embodiments, the method of identifying a peptide includes identifying the peptide using a de novo sequencing algorithm by exploiting a number of similarities and a number of differences between the first set of mass spectral data and the second set of mass spectral data, wherein the number of similarities arise from the presence of related peaks associated with a predetermined mass difference or sum. In one embodiment, the predetermined mass difference is 25.98 Da. In another embodiment, the predetermined mass difference is 29.03 Da, 28.03 Da, 42.04 Da, 55.01 Da, 54.01 Da, or 68.02 Da. In yet another embodiment, the predetermined mass sum is equal to M−1.01 Da, M+26.99 Da, M+28.02 Da, M+56.01 Da, M+27.02 Da, M+41.02, M+55.02 Da, or M+69.02, where M is a known peptide ion mass.

In illustrative embodiments, identifying the peptide using the de novo sequencing algorithm includes pairing a first value from the first set of mass spectral data with a second value from the second set of mass spectral data, wherein the first value is at a predetermined mass spacing different from the second value. In one embodiment, the predetermined mass spacing is the difference between (i) an $x_n$ fragment and an $y_n$ fragment, (ii) a $v_{n+1}$ fragment and the $x_n$ fragment, (iii) a $w_{n+1}$ fragment and the $x_n$ fragment, (iv) the $v_{n+1}$ fragment and the $y_n$ fragment, or (v) the $w_{n+1}$ fragment and the $y_n$ fragment, wherein n is the number of residues from a C terminus of the peptide. In another embodiment, the predetermined mass spacing is the sum of (i) an $a_n$ fragment and an $x_{N-n}$ fragment, (ii) a $b_n$ fragment and the $x_{N-n}$ fragment, (iii) the $a_n$ fragment and an $v_{N-n+1}$ fragment, (iv) the $b_n$ fragment and the $v_{N-n+1}$ fragment, (v) the $a_n$ fragment and an $w_{N-n+1}$ fragment, or (vi) the $b_n$ fragment and the $w_{N-n+1}$ fragment, wherein n is the number of residues from a C terminus of the peptide.

In illustrative embodiments, identifying the peptide using the de novo sequencing algorithm includes pairing a first value from the first set of mass spectral data with a second value from the second set of mass spectral data. For example, the first value is 25.98 Da greater than the second value. In another embodiment, the method further includes guanidinating a peptide. In another embodiment, the peptide is a tryptic peptide from a digestion of a protein. In yet another embodiment, the method includes assigning a C-terminal residue as arginine if 175.12 Da is in the second set of mass spectral data. In another embodiment, the method includes assigning a C-terminal residue as guanidinated lysine if 189.13 Da is in the second set of mass spectral data.

In illustrative embodiments, the method of identifying a peptide using the de novo sequencing algorithm includes establishing an order and an identity of amino acids in the peptide by comparing an amino acid molecular weight to a difference value between a subset of two values from the second set of mass spectral data independent of whether the subset of two values is found in the first set of mass spectral data.

In illustrative embodiments, a method of sequencing a polypeptide comprises digesting the polypeptide to form peptides, ionizing the peptides to form a population of peptide ions, fragmenting the population of peptide ions with high-energy photodissociation to form a population of fragments, obtaining a first mass spectrum of the population of fragments, obtaining a reference mass spectrum, identifying a population of low-energy fragments and a population of high-energy fragments by exploiting a predetermined relationship between the first mass spectrum and the reference mass spectrum, and sequencing the polypeptide with an algorithm based on mass differentials between a number of identified fragments. In one embodiment, fragmenting the population of peptide ions comprises exciting one or more α-carbon-carbonyl carbon bonds present in the peptide ions with a source of vacuum ultraviolet radiation at a wavelength of between about 100 and about 200 nm and at an energy sufficient to fragment the peptide ions by breaking at least one of the one or more α-carbon-carbonyl carbon bonds present therein.

In illustrative embodiments, exploiting the predetermined relationship between the first mass spectrum and the reference mass spectrum includes pairing a y-type ion present in the reference mass spectrum with an x-type ion present in the first mass spectrum. In yet another embodiment, exploiting the predetermined relationship between the first mass spectrum and the reference mass spectrum includes pairing an a-type ion present in the reference mass spectrum with an x-type ion present in the first mass spectrum. In another embodiment, exploiting the predetermined relationship between the first mass spectrum and the reference mass spectrum includes pairing an a-type ion present in the reference mass spectrum with a b-type ion present in the first mass spectrum. In another embodiment, a method of sequencing a polypeptide uses immonium ions for amino acid identification. In another embodiment, the method comprises exciting one or more α-carbon-carbonyl carbon bonds present in the peptide ions with a source of vacuum ultraviolet radiation at a wavelength of 157 nm. In another embodiment, the method comprises exciting one or more α-carbon-carbonyl carbon bonds present in the peptide ions with a source of vacuum ultraviolet radiation at a wavelength of 193 nm.

DETAILED DESCRIPTION

Figure 1A:
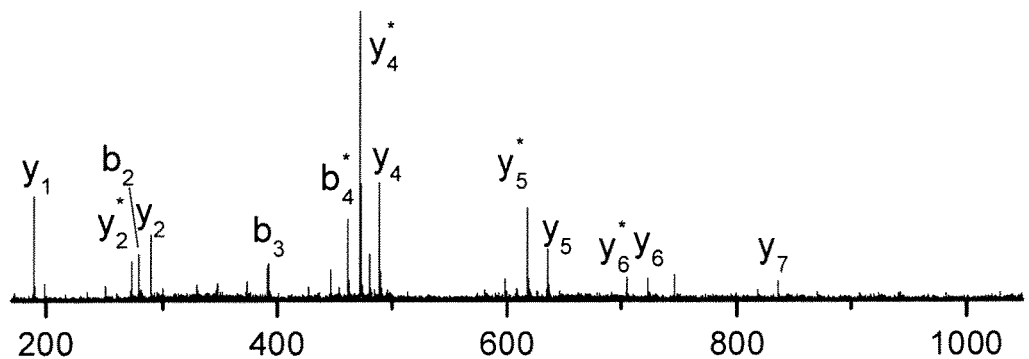
FIG. 1(A) shows a photodissociation spectrum of a peptide, SEQ. ID NO. 6 (MFLSFPTTK) after guanidination.

De novo sequencing methods have been developed to derive peptide sequences from tandem mass spectra without reference to a database. In one aspect, de novo sequencing algorithms may identify amino acids using mass differentials between consecutive peaks in tandem mass spectra. For example, algorithms have been developed to interpret low-energy collision-induced dissociation (CID) spectra. See, e.g. Taylor, J. A.; Johnson, R. S. *Anal. Chem.* 2001, 73, 2594-2604; Zheng, Z. Q. *Anal. Chem.* 2004, 76, 6374-6383; Bern, M.; Goldberg, D. *J. Comput. Biol.* 2006, 13, 364-378; Frank, A.; Pevzner, P. *Anal. Chem.* 2005, 77, 964-973; Fischer, B.; Roth, V.; Roos, F.; Grossmann, J.; Baginsky, S.; Widmayer, P.; Gruissem, W.; Buhmann, J. M. *Anal. Chem.* 2005, 77, 7265-7273; Ma, B.; Zhang, K. Z.; Hendrie, C.; Liang, C. Z.; Li, M.; Doherty-Kirby, A.; Lajoie, G. *Rapid Commun. Mass Spectrom.* 2003, 17, 2337-2342. Most proceed through two major steps. First, a pool of sequence candidates is generated based on peak mass differentials. One method for sequence generation employs the principles of graph theory in which a spectrum graph is created and paths that connect a number of peaks represent peptide sequences See, e.g., Mo, L. J.; Dutta, D.; Wan, Y. H.; Chen, T. *Anal. Chem.* 2007, 79, 4870-4878. According to this method, different series of fragment ions may not be differentiated by conventional algorithms. Accordingly, a large number of sequence candidates may be created. Second, a scoring algorithm may be designed to rank the derived sequence candidates and then the top ranking sequence is considered to be the correct sequence. Since scoring approaches aim to identify the best sequence from a pool of candidate sequences, the generated scores may represent some measure of the confidence level of a derived sequence. De novo sequencing directly identifies peptides from organisms without a database and provides an alternative approach for protein identification by sequence homology comparison when a database is available. The latter can also be used to evaluate the accuracy of de novo sequencing results.

Despite its advantages, de novo sequencing has not become a routine protocol to interpret proteomic data. One reason is that proteomic data interpretation relies on a series of fragment ions that extend through each peptide sequence. However, since low-energy CID of peptides induces preferential backbone cleavages, most CID spectra are dominated by a limited number of peaks that correspond to cleavage of weak bonds. As a result, only portions of peptide sequences may be derived. A second aspect of de novo sequencing is that most tandem mass spectra contain multiple series of ions. For example, both b- and y-type ions appear in low-energy CID spectra and until a peptide is actually identified, there may be no simple way to distinguish them. Confusion of these two ion series may lead to incorrect sequences when the spacing between two peaks happens to match the mass of an amino acid. According to a recent assessment of several de novo sequencing software packages, only 66% or fewer of the amino acids in peptide sequences were correctly identified in the analysis of tryptic peptides from model proteins using low-energy CID or TOF-TOF CID; the remaining residues were incorrectly assigned. See e.g., Huang, Y.; Triscari, J. M.; Tseng, G. C.; Pasa-Tolic, L.; Lipton, M. S.; Smith, R. D.; Wysocki, V. H. *Anal. Chem.* 2005, 77, 5800-5813.

Several peptide derivatization methods have been developed to distinguish different fragment ion series. See e.g., Brancia, F. L.; Montgomery, H.; Tanaka, K.; Kumashiro, S. *Anal. Chem.* 2004, 76, 2748-2755. In these methods, samples are divided into two fractions. Peptides in one fraction are labeled at their N- or C-terminus while peptides in the other fraction are unmodified. As a result, only fragment ions that carry the label are shifted in mass between the two spectra and N- and C-terminal fragments can thus be distinguished. Splitting the sample may cause a loss in sensitivity.

In an alternative approach, complementary CID and electron-capture dissociation (ECD) MS/MS spectra with an LTQ-FT mass spectrometer may be used. Peptides of interest may be first fragmented by low-energy CID in the linear ion trap and then dissociated by ECD in the FT-ICR mass spectrometer. See e.g., Savitski, M. M.; Nielsen, M. L.; Kjeldsen, F.; Zubarev, R. A. *J. Proteome Res.* 2005, 4, 2348-2354. In contrast with CID, ECD spectra are dominated by c- and z•type ions. Since the c-type ions are 17 Da heavier than the b-type ions while the z•type ions are 16 Da lighter than y-type ions, they provide so-called "golden complementary pairs". See e.g., Nielsen, M. L.; Savitski, M. M.; Zubarev, R. A. *Mol. Cell. Proteomics* 2005, 4, 835-845. Based on these distinctive mass spacings, b- and y-type ions in CID spectra can be distinguished. Combination of two complementary sets of data also increases sequence coverage of fragment ions. However, ECD is inoperable with MALDI instruments because ECD requires multiply-charged precursor ions.

A third issue for de novo sequencing is that amino acid assignments are not usually checked except by comparison with a protein sequence database. A preferred approach would be to employ multiple series of fragment ions. For example, observation of b- and y-type ion pairs adds confidence to amino acid assignments. However, low-energy CID rarely produces both b- and y-type ions at every amino acid and the two ion types are difficult to distinguish.

Differentiation of isobaric amino acids is another challenge for peptide de novo sequencing. Leucine and isoleucine are not distinguished by most de novo sequencing algorithms. This is not a trivial matter since these two amino acids account for 16.4% of all amino acids and their abundance is even higher in transmembrane proteins. Differentiation of leucine and isoleucine requires side-chain fragmentation, which is induced by high-energy CID in a sector instrument or high-energy ECD in a FT-ICR mass spectrometer, but not by low-energy CID. Likewise, there are two other pairs of amino acids with similar masses: lysine (128.0950 u) and glutamine (128.0589 u) as well as phenylalanine (147.0684 u) and oxidized methionine (147.0354 u). Although these residues are readily distinguished by high-resolution FT-ICR mass spectrometers and usually in TOF instruments, they are hardly separated by ion traps. Lysine can be guanidinated to distinguish it from glutamine. However, differentiation of phenylalanine and oxidized methionine remains a challenge for low-resolution mass spectrometers.

It has been demonstrated that UV photodissociation of singly-charged peptides yields high-energy fragments. For example, 157 nm photodissociation of singly-charged peptides yields abundant high-energy fragments. Reference is made to U.S. Pat. No. 7,618,806, which patent is hereby incorporated by reference herein in its entirety.

Figure 4:
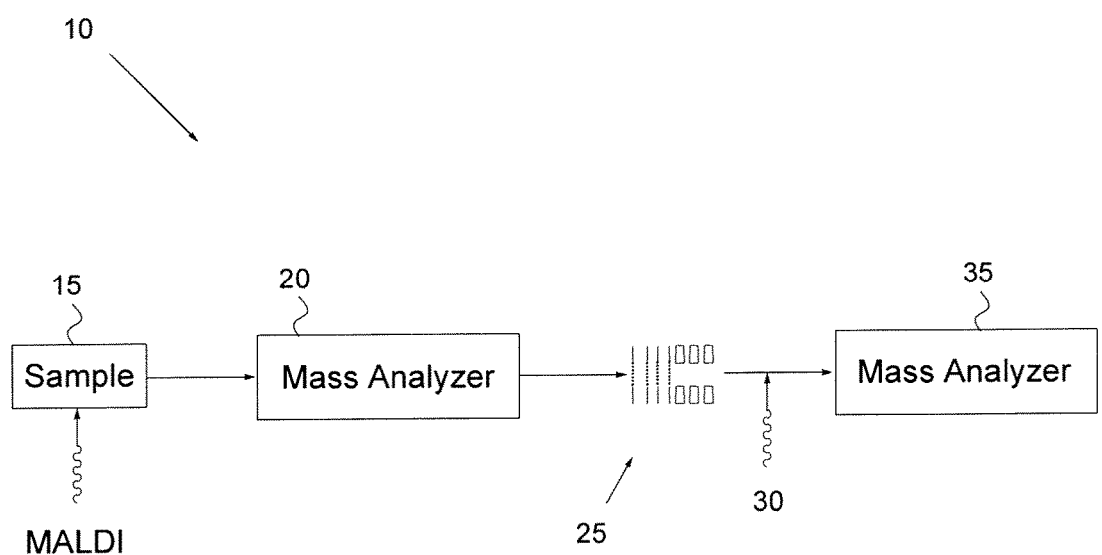
FIG. 4 shows an illustrative apparatus 10 for analyzing high molecular weight compounds by fragmentation.

An apparatus 10 suitable for yielding high-energy fragments is includes the components and features shown in FIG. 4. The apparatus may be used for analyzing large molecular complexes and/or high molecular weight compounds, including peptides, proteins, enzymatic digests of proteins, carbohydrates, glycopeptides, glycoproteins, nucleic acids, synthetic polymers, and the like. Referring to FIG. 4, the apparatus may be adapted from a conventional instrument that employs collision cells (See, K. F. Medzihradsky et al., *Anal. Chem.* 72:552 (2000), the disclosure of which is incorporated herein by reference. The adaptation includes a device that causes or induces ion fragmentation using a source of vacuum ultraviolet (VUV) laser light. In one aspect, precursor or molecular ions are generated by MALDI from sample 15, and those ions are accelerated into a first mass analyzer 20. First mass analyzer 20 optionally includes an ion trap or a reflectron TOF (not shown). In variations where first mass analyzer 20 is a time of flight analyzer, a linear flight tube (not shown) may also be included. In one illustrative aspect, the ions are separated in first mass analyzer 20. During this first stage, post-source decay (PSD) ions are formed by unimolecular dissociation and continue to travel with the precursor ion. See, R. Kaufmann, D. Kirsch, B. Spengler, Int. *J. Mass Spectrom. and Ion Proc.* 131:355 (1994). At the end of this first stage, one or more particular ions and/or its fragments are selected by ion gate 25 and then irradiated with a synchronized pulse of a predetermined wavelength of laser light at a predetermined energy from laser source 30. While the first mass analyzer 20 can be an ion trap or a reflectron TOF, one skilled in the art will appreciate that PSD ions may not be present in these analyzers.

In variations of the configuration shown in FIG. 4, ions exiting first mass analyzer 20 are sampled or selected by accelerating the ions in an orthogonal direction to the flow from first mass analyzer 20, rather than in a direction co-linear or parallel to the flow from first mass analyzer 20. Therefore, ion gate 25 is oriented perpendicular to the flow through first mass analyzer 20 allowing selected ions to be selectively located for acceleration. It is appreciated that such transverse or orthogonal configurations may improve overall performance of apparatus 10, and improve resolution.

The precursor ions and fragments thereof are then reaccelerated into a second stage of the apparatus that includes a mass analyzer 35, where each is separated and detected, optionally with isotopic resolution obtained for both the parent and fragment ions. In one illustrative aspect, mass analyzer 35 is a reflectron time-of-flight mass analyzer; however, it is appreciated that other mass analyzers, including but not limited to linear time of flight (LTOF), time of flight (TOF), triple-quadrupole, magnetic sector, quadrupole time-of-flight (Q-TOF), Fourier transform ion cyclotron resonance mass analyzers may be used in contemplated variations of the apparatus 10. In another illustrative aspect, laser source 30 is a molecular fluorine ($F_2$) laser. In one illustrative variation, the $F_2$ laser is operated on alternating MALDI shots. In this variation, it is appreciated that the post-source decay fragments may be more easily distinguished from those generated by photodissociation by subtraction of the signals generated from alternate MALDI shots. In another variation, 2,5-dihydroxybenzoic acid (DHB) is used as a matrix for photodissociation experiments. It is further appreciated that a 2,5-dihydroxybenzoic acid (DHB) matrix may minimize the production of post-source decay fragments, as reported by B. Spengler, D. Kirsch, R. Kaufmann, in *J. Phys. Chem.* 96, 9678 (1992), the disclosure of which is incorporated herein by reference. It is understood that an α-cyano-4-hydroxycinnamic acid (CHCA) matrix may be used to deliberately generate PSD fragments. It is further understood that a CHCA matrix may also be used for photodissociation if background subtraction of PSD data is performed. It is appreciated that other matrices or additives may also be used in variations of the embodiments described herein, such as cinnamic acid analogs and derivatives like ferulic acid, sinapinic acid, and the like, hydroxypicolinic acid, and other matrices.

In another embodiment, the first mass analyzer 20 is an ion trap capable of separating and detecting the low-energy fragments. According to this embodiment, the first mass analyzer can further include a source of VUV laser light. One or more particular ions and/or its fragments are selected by the ion trap and then irradiated with a synchronized pulse of a predetermined wavelength of laser light at a predetermined energy from a laser source incident on ions trapped in the first mass analyzer. The first mass analyzer can then be subsequently used as the second stage mass analyzer 35.

In another aspect, the predetermined wavelength is chosen to selectively or specifically excite particular bond types present in the molecules under analysis. In another aspect, the predetermined energy is chosen to be sufficiently high to cause selective or specific breakage of particular bond types in the molecules under analysis.

Illustratively, the molecules under analysis are peptides and/or proteins, including high molecular weight peptides and/or proteins. Illustrative wavelengths are less than about 190 nm. In variations, illustrative wavelengths are selected within the range from about 130 nm to about 175 nm, and/or within the range from about 155 nm to about 160 nm. Illustrative energies are at least about 5 eV, within the range from about 5 eV to about 9 eV, and/or within the range from about 7.5 eV to about 8.5 eV. Another illustrative energy and wavelength is about 1 mJ of about 157 nm (7.9 eV photon energy) light produced from a molecular fluorine ($F_2$) laser. However, it is to be understood that higher energy photons are also contemplated, including energies that are much greater than about 5 eV, such as about 12 eV or greater, or about 20 eV or greater.

Any of a wide variety of light sources capable of producing the predetermined wavelengths along with the predetermined energies is contemplated herein, including but not limited to laser light sources, other vacuum ultraviolet lasers, and beams of coherent light generated through non-linear optical methods. Incoherent light produced by a synchrotron or created, for example, in electrical discharges may also be used to induce ion photodissociation in the methods, devices, and apparatus described herein. It is appreciated that light produced by a synchrotron may be at very high energy, such as light having a wavelength of about 50 nm or even less. Such high energy light is contemplated, and may be used in the methods, devices, and apparatus described herein.

In illustrative embodiments, a device for fragmenting a peptide ion or protein ion substantially at one or more of the α-carbon-carbonyl carbon bonds present in the peptide ion or protein ion comprises a first component capable of forming the peptide ion or protein ion from a sample, a second component which is different from the first component comprising a source of vacuum ultraviolet radiation adapted to deliver light at an energy sufficient to break at least one of the one or more α-carbon-carbonyl carbon bonds and produce one or more fragments of the peptide ion or protein ion, and a third component comprising a first mass analyzer, where the mass analyzer is operably connected to receive the one or more fragments of the peptide ion or protein ion. In one embodiments, the vacuum ultraviolet radiation has a wavelength of about 157 nm. In another embodiment, the source of vacuum ultraviolet radiation is a laser. In another embodiment, the component capable of forming the peptide or protein ion from a sample is an electrospray device. In yet another embodiment, the device further includes a fourth component comprising a second mass analyzer. In one embodiment, the first mass analyzer is a time of flight mass analyzer. In another embodiment, the second mass analyzer is a time of flight mass analyzer.

In illustrative embodiments, the device further includes an ion trap adapted for trapping the peptide ion or protein ion prior to fragmentation. In one embodiment, the ion trap is coupled to the second mass analyzer. In yet another embodiment, the device further includes a fifth component for measuring the mass/charge ratio of the one or more fragments.

Theoretical and spectroscopic studies of small polypeptides suggest that they absorb rather strongly in the vacuum ultraviolet (VUV) region of the spectrum, and the chromophore involved in the process is associated with the peptide backbone amides. See, e.g., J. W. Price, R. Setlow, *J. Chem. Phys.* 25:138 (1956). A strong band occurs near 190 nm, and this transition can be excited using 193 nm ArF laser light. See, e.g., D. L. Peterson, W. T. Simpson, *J. Am. Chem. Soc.* 79:2375 (1957). In addition, the 6.4 eV photon energy of ArF laser light is similar to that imparted in ECD. However, photodissociation experiments at this wavelength generally produce the common b and y fragments that are indicative of energy randomization. In addition, and in contrast to vibrational excitation methods, some non-specific side chain fragmentation is also observed with this method.

Figure 5:
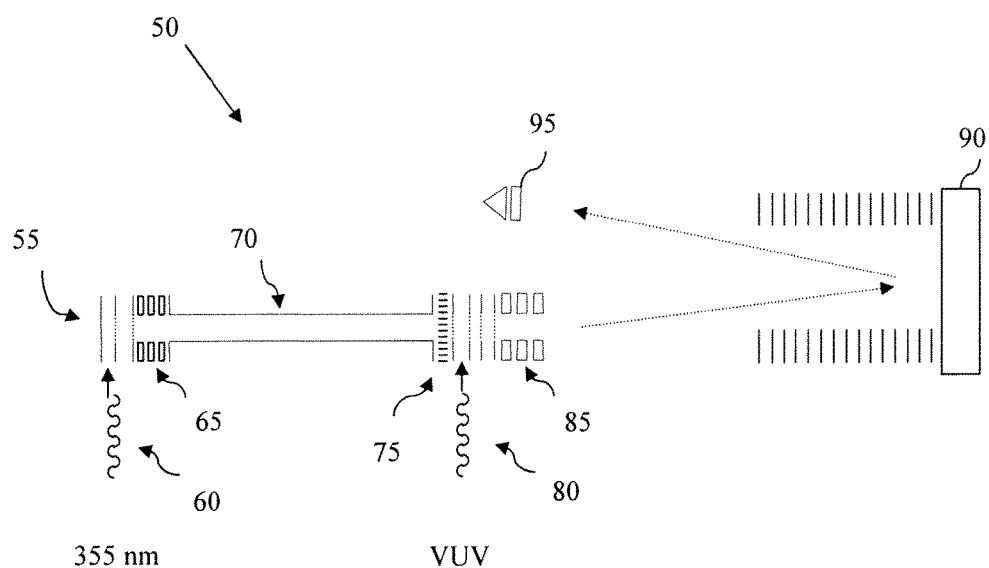
FIG. 5 shows an illustrative apparatus 50 for analyzing high molecular weight compounds by fragmentation.

In another illustrative embodiment, a device 50 representing a TOF-TOF instrument is described and includes the components and features shown in FIG. 5. Referring to FIG. 5, a sample, such as a peptide, protein, protein digest, and the like enters through inlet 55 and is irradiated with a first source of light 60, which illustratively may be laser light. The first source of laser light is illustratively at a wavelength and energy sufficient to convert molecules in the sample into molecular or precursor ions. Illustratively, the wavelength is about 355 nm. In one variation, the ions are produced from the sample using MALDI; however, other initial ionization methods may be used in variations of the device 50. The precursor or molecular ions enter focusing lens 65 coupled to linear flight tube 70. In variations of this configuration, the focusing lens is coupled to a mass selecting component, including but not limited to a quadrupole device. The mass selecting component selects certain predetermined mass values and accelerates those ion masses into linear flight tube 70. Linear flight tube 70 is coupled to ion gate 75, which allows predetermined mass values to exit ion trap 70. Those ion masses are contacted with a second source of light 80, which illustratively may be laser light, emitting radiation at a predetermined wavelength and having a sufficient energy to cause photodissociation of predetermined bonds in the ion masses leading to fragmentation. The resulting fragmented ion masses are accelerated through focusing lens 85 into a mass analyzer, such as a reflecting time of flight component 90 to detector 95.

In variations of the configuration shown in FIG. 5, the sample entering inlet 55 is ionized using another conventional component, including electrospray, sonic spray, electro-sonic spray, fast atom bombardment, and the like. It is appreciated that such ionization of the sample is advantageously performed to minimize fragmentation, in order that the primary fragmentation pattern observed is accomplished by the second source of laser light 80. In other variations of the configuration shown in FIG. 5, ions exiting linear flight tube 70 are sampled or selected by accelerating the ions in an orthogonal direction to the flow from linear flight tube 70, rather than in a direction co-linear or parallel to the flow from linear flight tube 70. Therefore, focusing lens 85 is oriented perpendicular to the flow through linear flight tube 70 allowing selected ions to be selectively located for acceleration. It is appreciated that such transverse or orthogonal configurations may improve overall performance of apparatus 50, and improve resolution.

In another illustrative embodiment, a variation of the device 50 shown in FIG. 5 is described, and represents another homebuilt MALDI tandem time of flight instrument. Precursor ions are separated in a linear TOF apparatus, and those precursor ions of interest are selected by an ion gate. An unfocused 10-ns, 2-mJ laser pulse with a cross section of 5 mm by 10 mm, and having a wavelength of about 157 nm VUV light generated from an $F_2$ laser, interacts with the selected ions. Precursor and fragment ions are then reaccelerated, separated, and detected in a reflectron TOF analyzer. Spectra with and without photodissociation are recorded on alternating shots so that the post source decay (PSD) contribution can be subtracted away. For comparison, high-energy collision-induced dissociation data can be recorded on an Applied Biosystems (Foster City, Calif.) 4700 Proteomics Analyzer using 2-keV fragmentation energy with air as the collision gas. Low energy CID can be performed on a Thermo Scientific LTQ using an atmospheric pressure MALDI ionization source. When peptides have a C-terminal arginine, a series of x-type ions along with numerous v- and w-type ions are primarily produced. Since the x-type ions extend through the peptide backbone, they can be used to derive peptide sequences directly.

Illustratively, in peptides generated by digesting proteins with the enzyme trypsin, the C-terminal residue will often be arginine or lysine. The presence of arginine at the C-terminus enhances the generation of x- and v-type fragments by 157 nm photodissociation, since arginine has the highest gas phase basicity of the amino acids. In contrast, because histidine has a higher gas phase basicity than lysine (Harrison, A. G., Mass Spectrom. Rev. 16, 201 (1997)), the charge will not always be sequestered at the C-terminus of lysine-containing tryptic peptides in peptide and peptide fragment ions that include both lysine and histidine. However, simple methods are available to increase the basicity of lysine residues, as described by R. L. Beardsley, J. P. Reilly, in Anal. Chem. 74, 1884 (2002); R. L. Beardsley, J. A. Karty and J. P. Reilly, J. Rapid Commun. Mass Spectrometry, 14, 2147 (2000), the disclosure of which is incorporated herein by reference. Such methods of increasing the basicity of lysine residues are contemplated in variations of the methods described herein. This increase in the basicity of lysine residues tends to improve the ionization efficiency of lysine-terminated peptides and increase the probability that most or all of the tryptic fragments resulting from complete digestion will produce C-terminal fragment ions. An alternative method for increasing the probability that most or all of these fragments are of the same type involves introducing a sulfonic acid group at the C-terminus; however, it is appreciated that this method may also reduce MALDI ionization efficiency. See, T. Keough, R. S. Youngquist, M. P. Lacey, Proc. Natl. Acad. Sci. USA 96, 7131 (1999).

In one illustrative variation, peptide digests that include a large number of C— and or N-terminal lysine residues may be further treated prior to analysis to convert the amino group of the lysine residue into a guanidino group. It is appreciated that such a conversion may increase the basicity of the lysine residues.

In another embodiment, methods and apparatus are described herein for sequencing peptides and/or proteins. In one aspect, trypsin digests, or other conventional enzymatic digests of peptides or proteins used for subsequent sequencing experiments form part of the methods. In one embodiment, any proteolytic enzyme may be used according to the methods disclosed herein. In another embodiment, the peptide could be amidinated or derivitized with a charge tag on the N-terminus. This approach would result in the formation of a-type and d-type fragments. The resulting mass spectra would be somewhat simpler in interpretation due to the relatively fewer distinct fragments that would result; however, this may result in increased difficulty in peak assignment due to the decreased redundancy in assignment. The algorithm for de novo sequencing data according to this embodiment would be analogous to the algorithm described in detail here but distinct in its reliance on different relationships between the low-energy fragments and high-energy fragments.

Enzymatic digests of such peptides and/or proteins are analyzed using mass spectrometric protein identification procedures, where these procedures include the methods and/or fragmentation devices described herein. In another aspect, the method includes a device or component capable of generating laser light at 157 nm for photodissociation of the peptides and/or proteins found in enzymatic digest, such as trypsin digests, and the like. The methods described herein are suitable for de novo peptide sequencing, allowing the direct interpretation of the fragmentation spectrum generated by the apparatus described herein. Such peptide sequences directly derived from mass spectrometric data identification are useful when appropriate database standards do not exist or contain database errors, or in cases where the peptide being analyzed has been mutated or post-translationally modified.

In illustrative embodiments, the methods described herein include the analysis of large and/or high molecular weight compounds. Illustrative large and/or high molecular weight compounds include, but are not limited to, peptides, proteins, carbohydrates, glycopeptides, glycoproteins, nucleic acids, synthetic polymers, and the like. In aspects of this embodiment, the methods described herein use a source of laser light that has a predetermined wavelength for fragmentation of the compound or molecule to be analyzed. The predetermined wavelength is illustratively selective or specific for a bond type present in the molecule to be analyzed. It is appreciated that fragmentation methods described herein may be based on selecting the predetermined wavelength that corresponds to a bond type that is present in large numbers in the molecule to be analyzed. Thus, diverse fragments are generated allowing the structure or sequence of the molecule to be determined. In another illustrative aspect, the molecule to be analyzed is a peptide or protein, and the predetermined wavelength is selective or specific for a backbone amide bond. In other aspects of this embodiment, the methods described herein use a source of laser light that has a predetermined energy that is sufficient for selectively or specifically breaking or cleaving the bond type present in the molecule to be analyzed. In another illustrative aspect, the molecule to be analyzed is a peptide or protein, and the predetermined energy is sufficient to selectively or specifically break or cleave a backbone amide bond.

In illustrative embodiments, any of a variety of methods for producing molecular ions are included prior to fragmentation using the methods described herein. Any suitable method for forming precursor ions, including but not limited to MALDI, electrospray (ES), sonic spray, electro-sonic spray, fast atom bombardment, and the like are contemplated. It is appreciated that depending on the molecules or compounds analyzed, these ion sources may produce singly charged ions, or multiply charged ions in some cases.

In illustrative embodiments, any of a variety of mass analyzers are contemplated for use with the methods described herein. Both precursor ions and photofragment ions can be isolated and identified using different types of mass analyzers, including but not limited to linear time of flight (LTOF), time of flight-time of flight (TOF-TOF), reflectron time of flight, linear ion trap-time of flight (LIT-TOF), triple-quadrupole, magnetic sector, quadrupole time-of-flight (Q-TOF), Fourier transform ion cyclotron resonance, linear, and 3D ion traps. The choice of the particular mass analyzers is made during routine optimization of the methods, devices, and apparatus described herein, with regard to sample compatibility, sensitivity, resolution, and other routinely optimized parameters. The ion photodissociation method is compatible with any of these mass analyzers. Some of these instruments have the capability of storing ions or performing higher order MS$^n$ experiments, which capabilities facilitate photofragmentation studies.

In illustrative embodiments, a de novo sequencing algorithm is described that automatically derives peptide sequences from photodissociation data. In one embodiment, the algorithm combines photodissociation and PSD data to identify x/y ion pairs or other pairs and derive peptide sequences. Spacings between adjacent a and b ions are commonly recognized by those of ordinary skill in the art because these two types of ions are often observed (e.g. $a_n-b_n=28.00$, where this n labels the number of residues from the N terminus of the peptide). However, because most peptide fragmentation experiments do not generate many x-, v- and w-type ions, the following relationships have not been used in a de novo sequencing algorithm to assign ion types: $x_n-y_n=25.98$, $v_{n+1}-x_n=29.03$, $w_{n+1}-x_n=28.03$ or 42.04, $v_{n+1}-y_n=55.01$, and $w_{n+1}-y_n=54.01$ or 68.02 (this n labels the number of residues from the C terminus of the peptide). Furthermore, this group of relationships is merely representative. Further relationships are within the scope of this application, although not specifically described.

The sum of the masses of complementary b and y ions are commonly recognized by those of ordinary skill in the art because these two types of ions are often observed (e.g. $b_n+y_{N-n}=M+1.01$, where N labels the total number of residues in the peptide and M is the mass of the peptide ion). The present disclosure describes how the sums of complementary fragment ion masses may be used in a de novo sequencing algorithm to assign ion types. In illustrative embodiments, $a_n+x_{N-n}=M-1.01$, $b_n+x_{N-n}=M+26.99$, $a_n+v_{N-n+1}=M+28.02$, $b_n+v_{N-n+1}=M+56.01$, $a_n+w_{N-n+1}=M+27.02$ or 41.02, and $b_n+w_{N-n+1}=M+55.02$ or 69.02 (where N labels the total number of residues in the peptide and M is the mass of the peptide ion) may be used to determine the identities of many peptide fragment ions.

In illustrative embodiments, observation of y-, v-, or w-type ions may provide additional constraints to assess the identity and or confidence of each residue assignment in a computed sequence. As described herein, photofragmentation is a high-energy ion fragmentation process; therefore, it tends to generate an abundance of immonium ions. The abundance of immonium ions may be used for identification; thus, observation of immonium ions may provide additional constraints to assess the identity and confidence of each residue assignment in a computed sequence.

In illustrative embodiments, a method of identifying a peptide comprises using a number of similarities and a number of differences between a first set of mass spectral data obtained from an instrument that generates high-energy fragments of the peptide and a second set of mass spectral data with a de novo sequencing algorithm to determine a sequence for the peptide, wherein the number of similarities arise from a presence of related peaks between the first set of mass spectral data and the second set of mass spectral data and the sequence can be used to identify the peptide. In one embodiment, the second set of mass spectral data was obtained from an instrument that generates low-energy fragments of the peptide. In another embodiment, the instrument that generates high-energy fragments of the peptide and the instrument that generates low-energy fragments of the peptide are the same instrument run in two operational modes. In yet another embodiment, the instrument that generates high-energy fragments of the peptide and the instrument that generates low-energy fragments of the peptide are not the same instrument. In another embodiment, the instrument that generates high-energy fragments of the peptide uses vacuum ultraviolet photodissociation to generate high-energy fragments. In another embodiment, the instrument that generates low-energy fragments of the peptide uses post-source decay following matrix assisted laser desorption ionization or collision-induced dissociation following electrospray ionization to generate low-energy fragments.

In illustrative embodiments, the method of identifying a peptide comprises establishing the presence of related peaks associated with a predetermined mass difference. In one embodiment, the predetermined mass difference is 25.98 Da. In another embodiment, the predetermined mass difference is 29.03 Da, 28.03 Da, 42.04 Da, 55.01 Da, 54.01 Da, and/or 68.02 Da. In one embodiment, the presence of related peaks is associated with a predetermined mass sum. In another embodiment, the predetermined mass sum is selected from the group consisting of M−1.01 Da, M+26.99 Da, M+28.02 Da, M+56.01 Da, M+27.02 Da, M+41.02 Da, M+69.02 Da, and M+55.02 Da, wherein M is a known peptide ion mass. Illustratively, the method of identifying the peptide using the de novo sequencing algorithm includes pairing a first value from the first set of mass spectral data with a second value from the second set of mass spectral data, wherein the first value is at a predetermined mass spacing different from the second value. For example, the predetermined mass spacing may be the difference between an $x_n$ fragment and an $y_n$ fragment, a $v_{1+1}$ fragment and the $x_n$ fragment, a $w_{n+1}$ fragment and the $x_n$ fragment, the $v_{n+1}$ fragment and the $y_n$ fragment, or the $w_{n+1}$ fragment and the $y_n$ fragment, wherein n is the number of residues from a C terminus of the peptide. In another example, the predetermined mass spacing is the sum of an $a_n$ fragment and an $x_{N-n}$ fragment, a $b_n$ fragment and the $x_N$, fragment, the $a_n$ fragment and an $v_{N-n+1}$ fragment, the $b_n$ fragment and the $v_{N-n+1}$ fragment, the $a_n$ fragment and an $w_{N-n+1}$ fragment, or the $b_n$ fragment and the $w_{N-n+1}$ fragment, wherein N is a total number of residues of the peptide and n is a number of residues from a C terminus of the peptide.

In illustrative embodiments, a method of sequencing a polypeptide includes obtaining a first mass spectrum of a population of fragment ions produced from ionizing peptides digested from the polypeptide with an instrument using high-energy photodissociation and a reference mass spectrum of a population of fragment ions produced from ionizing peptides digested from the polypeptide with an instrument using low-energy fragmentation, identifying a population of low-energy fragments and a population of high-energy fragments by exploiting a predetermined relationship between the first mass spectrum and the reference mass spectrum, and sequencing the polypeptide with an algorithm based on mass differentials between a number of identified fragments. In one embodiment, the instrument using high-energy photodissociation excites one or more α-carbon-carbonyl carbon bonds present in the peptide ions with a source of vacuum ultraviolet radiation at a wavelength of between about 100 and about 200 nm and at an energy sufficient to fragment the peptide ions by breaking at least one of the one or more α-carbon-carbonyl carbon bonds present therein. In another embodiment, exploiting the predetermined relationship between the first mass spectrum and the reference mass spectrum includes pairing a y-type ion present in the reference mass spectrum with an x-type ion present in the first mass spectrum. In another embodiment, exploiting the predetermined relationship between the first mass spectrum and the reference mass spectrum includes pairing an a-type ion present in the reference mass spectrum with an x-type ion present in the first mass spectrum. In yet another embodiment, exploiting the predetermined relationship between the first mass spectrum and the reference mass spectrum includes pairing a low-energy fragment peak present in the reference mass spectrum with a high-energy fragment peak present in the first mass spectrum, the low-energy fragment peak differing from the high-energy fragment peak by a mass selected from the group consisting of 25.98 Da, 29.03 Da, 28.03 Da, 42.04 Da, 55.01 Da, 54.01 Da and 68.02 Da. In yet another embodiment, obtaining the first mass spectrum of the population of fragment ions produced from ionizing peptides digested from the polypeptide with the instrument using high-energy photodissociation includes exciting one or more α-carbon-carbonyl carbon bonds present in the peptide ions with a source of vacuum ultraviolet radiation at a wavelength of 157 nm. In another embodiment, the source of vacuum ultraviolet radiation has a wavelength of 193 nm.

Following are illustrative exemplified embodiments of the present disclosure. The following examples are intended to illustrate various embodiments of the invention, and are not intended and should not be interpreted to limit the invention in any way. For example, the exemplified embodiments described herein were performed on a MALDI tandem time-of-flight instrument. Nevertheless, it is to be understood that these exemplified embodiments as well as the other illustrative embodiments of the invention described herein are equally applicable to the full range of other homebuilt and/or commercially available mass spectrometers in contemplated variations of the invention.

EXAMPLES

Materials.

Human hemoglobin, horse myoglobin, horse cytochrome C and bovine ubiquitin were purchased from Sigma (St. Louis, Mo.). Acetonitrile (ACN) and trifluoroacetic acid (TFA) were obtained from EMD Chemicals, Inc. (Gibbstown, N.J.). α-cyano-4-hydroxycinnamic acid (CHCA) were bought from Sigma (St. Louis, Mo.). O-methylisourea was purchased from Acros Organics (NJ). Trypsin was obtained from Sigma (St. Louis, Mo.). Ammonium bicarbonate (ABC) was purchased from Sigma (St. Louis, Mo.).

Tryptic Digestion.

Tryptic peptides from human hemoglobin, horse myoglobin, horse cytochrome C and bovine ubiquitin were generated using bovine trypsin. Each protein was prepared in 25 mM ammonium biocarbonate to make a concentration of 100 uM. Tryptic digestion was performed by mixing 100 uL of each protein solution with 5 ug lyophilized trypsin. The digestion was allowed to incubate at 37° C. overnight before being stored at −20° C. To build a library of peptides, a total of 23 proteins listed in Table 1 were digested with trypsin. For the 20 proteins with a limited number of disulfide bonds, tryptic digestion was performed following the procedure described above. For three proteins that contain many disulfide bonds, the employed digestion procedure was adopted from previous work by Reilly and coworkers, in which disulfide bonds were first chemically reduced and cysteine residues were then alkylated before enzymatic digestion (See, Beardsley, R. L.; Sharon, L. A.; Reilly, J. P. Anal. Chem. 2005, 77, 6300-6309). Proteins shown in bold were digested after disulfide bond reduction and cysteine; others were digested as described herein.

TABLE 1

Proteins for generation a tryptic peptide library

| Name | Species | UniProtKB accession # | Mass (kDa) | # of disulfide bonds |
|---|---|---|---|---|
| α-Casein (dephosphorylated) | Bovine | P02663 | 26 | 0 |
| α -Casein | Bovine | P02663 | 26 | 0 |
| Carbonic anhydrase | Bovine | P00921 | 28.8 | 0 |
| Ovalbumin | Chicken | P01012 | 42.9 | 1 |
| Ribonuclease A | Bovine | P61823 | 16.5 | 4 |
| β-Casein | Bovine | P02666 | 25.1 | 0 |
| Concanavalin A | Jack Bean | P02866 | 31.4 | 0 |
| Deoxyribonuclease I | Bovine | P00639 | 31.3 | 2 |
| Pepsin | Porcine | P00791 | 41.2 | 3 |
| Catalase | Bovine | P00432 | 59.5 | 0 |
| Phosphoglucose Isomerase | Yeast | P12709 | 61.3 | 0 |
| α -Amylase | Bacillus | Q2MKJ7 | 58.4 | 0 |
| Protease, type X | Bacillus | P00800 | 60.1 | 0 |
| Lysozyme | Chicken | P00698 | 16.2 | 4 |
| Hemoglobin | Human | | 31.2 | 0 |
| Myglobin | Horse | P68082 | 17.1 | 0 |
| Ubiquitin | Bovine | P62990 | 85.6 | 0 |
| Cytochrome C | Horse | P62894 | 11.7 | 0 |
| Albumin | Bovine | P02769 | 69.3 | 17 |
| α -Casein | Bovine | P02663 | 26 | 0 |
| Carbonic anhydrase | Bovine | P00921 | 28.8 | 0 |
| Ovalbumin | Chicken | P01012 | 42.9 | 1 |
| Ribonuclease A | Bovine | P61823 | 16.5 | 4 |

Peptide Guanidination.

Tryptic peptides were guanidinated using O-methylisourea (See e.g., Beardsley, R. L. and J. P. Reilly Anal. Chem. 2002, 74, 1884). Guanidination reagent solution was made by dissolving 0.05 g O-methylisourea in 51 uL water. For each derivatization, 5 uL of peptide solution was mixed with 5.5 uL ammonium hydroxide (7 N) and 1.5 uL of the guanidination reagent. The pH of reaction solutions was about 10.6. The reaction was incubated at 65° C. for 5-10 minutes before being terminated by adding 15 uL 10% TFA (VAT). Reaction mixtures were dried by a speed vac before being stored at −20° C.

Sample Preparation for MALDI Analysis.

Guanidinated peptides were resuspended in water to make 10 uM solutions and were desalted by homemade microextraction zip-tip columns packed with C18-derivatized silica gel (Grace Vydac, Hesperia, Calif.) before MALDI analysis. In a typical experiment, 10 g/L CHCA in 49.95% ACN and 49.95% H₂O with 0.1% TFA was prepared as the matrix solution. 1 uL aliquots of peptide solutions were loaded onto zip-tip columns. After being washed by 0.1% TFA in water, peptides were released into 2 uL matrix solution. MALDI spots were made by depositing 0.5 uL aliquots of the peptide-matrix mixture onto a plate. For each peptide, two MALDI spots were created.

Mass Spectrometry.

Photodissociation and PSD were performed on an ABI 4700 TOF-TOF mass spectrometer (Applied Bio systems, Framingham, Mass.). In brief, photodissociation was implemented using an F₂ laser (CompexPro F₂, Coherent Lambda Physik, Germany). The laser was attached to the collision cell through a feed-through in the TOF-TOF main chamber. A computer program was developed to coordinate the photodissociation laser with the mass spectrometer. Peptide masses were first measured in the MS mode. Photodissociation timings were then calculated by the computer program. In the MSMS mode, peptide ions of interest were isolated by a timed ion gate. When the ion packet arrived at the photodissociation spot, a programmable delay generator (BNC model 555, Berkeley Nucleonics Corporation, San Rafael, Calif.) was then used to trigger the laser based on the calculated timing. A 10 mJ, 10 nanosecond pulse of light (19 mm high by 6 mm wide) was typically produced. The precursor ions as well as the PSD fragments were photoexcited. The resulting photofragments along with the remaining precursor ions and PSD fragments were then reaccelerated into the reflectron-TOF for mass analysis. Peptide PSD spectra were obtained with the photodissociation laser switched off. Currently this apparatus runs at 50 Hz because this is the maximum repetition rate of the $F_2$ laser.

All tryptic peptide mixtures from model proteins were first analyzed without fragmentation to obtain a list of precursor ion masses. The top 10 strongest peaks from each mass spectrum were isolated for photodissociation. Each photodissociation spectrum was recorded by averaging 2000 MALDI shots (about 40 seconds). PSD spectra were also recorded by averaging 2000 MALDI shots with the same MALDI laser intensity applied in the photodissociation experiments. All spectra were processed in Data Explorer version 3.0 (Applied Biosystems, Framingham, Mass.) and then plotted by Origin version 7.0 (OriginLab, Northampton, Mass.). Peptide fragment masses were predicted using Protein Prospector (http://prospector.ucsf.edu).

Preliminary Data Processing.

All photodissociation and PSD spectra were smoothed and corrected to zero baseline using Data Explorer. All monoisotopic peaks with a signal-to-noise ratio (S/N) greater than 15 were detected by the ABI 4000 Explorer software. Within every 200 Da mass window, a maximum of 10 peaks were selected for output based on their intensities. In total, a maximum of 100 peaks were exported. Along with the precursor mass, a list of mass-to-charge ratios (m/z) and peak intensities of the selected fragments was stored in an ASCII file. Photodissociation and PSD peak lists were stored in two separate files. These text files were processed using in-house software programmed with Visual Basic (Microsoft, Seattle, Wash.) as follows. First, PSD fragments in photodissociation spectra were identified by alignment with PSD spectra. Peaks that occur in both were labeled as PSD fragments; otherwise, they were considered to be photofragments. Second, x-type ions are 25.98 Da heavier than corresponding y-type ions. Thus any photofragments that were 25.98 Da heavier than PSD fragment were tentatively labeled as x-type ions and the PSD fragments were labeled as y-type ions. Third, although $x_1$ ions were sometimes not observed, $y_1$ ions almost always were detected. Therefore, if a 175.12 or 189.13 Da $y_1$ ion (corresponding to arginine or guanidinated lysine) was observed, the C-terminal residue was established.

De Novo Sequencing Algorithm.

The algorithm uses x-type ions to derive peptide sequences. The computation routine includes two major steps: deriving tentative sequences and checking for errors. The algorithm first constructs a rough sequence using the putative x/y ion pairs. When mass spacings between two x-type ions match the mass of an amino acid, the corresponding amino acid is tentatively assigned; otherwise, a gap is produced. To bridge two gapped x/y ion pairs, the algorithm then looks for possible x-type ions based on peak mass spacings. This routine starts from the smaller x-type ion in a gapped x/y ion pair and measures the mass spacing between it and all peaks within 186.5 Da (which is just above the mass of the heaviest amino acid). When a spacing matches the mass of an amino acid, the peak is labeled as a tentative x-type ion and the corresponding amino acid is tentatively assigned. When multiple x-type ions are found, each amino acid assignment leads to an individual sequence and multiple tentative sequences are generated.

These assignments are subsequently checked by the spacing to the next x- or y-type ion. If the spacing matches the mass of an amino acid, the assignment is considered to be correct; otherwise, it is false and is removed. If no x-type ions are found, the algorithm looks for possible y-type ions based on peak mass spacings from y-type ions in the gapped x/y ion pairs. When neither an x- nor a y-type ion is found, the size of the mass gap is simply listed. After tentative residue assignments are completed, sequences are examined by observation of v-, w- and y-type ions that are then used to check these assignments. Confidence levels for amino acids are determined based on the occurrence of constraint ions that are terminated by these residues. When an x/y ion pair is observed, the assignment is rewarded with the highest confidence score of 1.0; otherwise, assignments are evaluated by how many of the x-, y-, v- and w-type ions are detected in photodissociation spectra relative to the number that could be formed. The average score of all amino acid assignments is then used to assess the credibility of a sequence. All tentative sequences are further ranked based on their confidence scores.

For peptide mixture analysis, peak lists from all photodissociation spectra are stored in a single file along with precursor mass information. PSD data are stored in a similar fashion. For each peptide, the de novo sequencing algorithm imports photodissociation and PSD peak lists along with precursor mass information to derive peptide sequences. The top 10 ranked sequences are usually output.

Homology Sequence Searching.

In order to evaluate the sequencing accuracy and test the method's capability for identifying proteins, de novo sequencing results were matched against a database using the MS-homology searching program publicly available from UCSF Mass Spectrometry Facility (http://prospector.ucsf.edu). Although this search engine accepts gapped sequences, gaps must be small corresponding to fewer than 50 possible amino acid combinations. Therefore before searches, all sequences were checked by an in-house computer program. Complete sequences and those with a small gap were unchanged. However for sequences with a large gap, only the longest consecutive amino acid assignments were output. Sequence matching was done assuming no enzyme specificity was employed during sequence matching. A mass tolerance of ±0.3 Da was applied for gap mass values. In order to test whether each derived peptide sequence identified a unique protein, the SwissProt.2008.06.10 database with 389046 protein entries was used as the search library. Exact sequence matching was initially attempted. Unmatched sequences were subjected to another search allowing for two incorrect amino acid assignments.

Combination of Photodissociation and PSD Data.

Figure 1B:
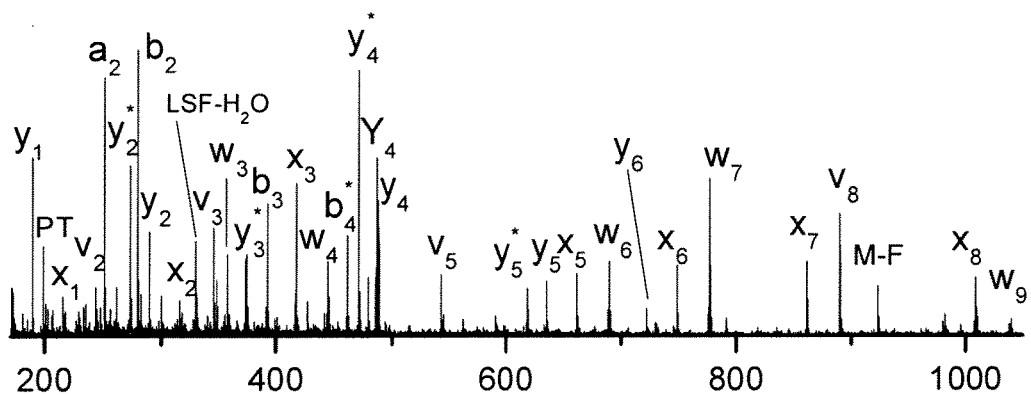
FIG. 1(B) shows a post-source decay spectrum of SEQ. ID NO. 6 after guanidination.
Figure 1C:
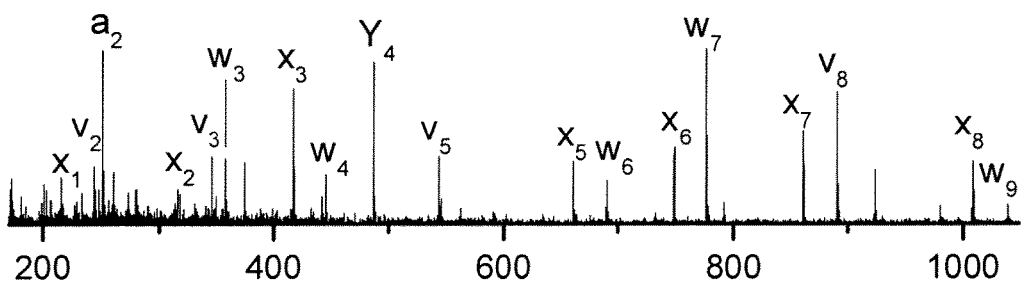
FIG. 1(C) shows photodissociation spectrum after removal of post-source decay fragments of SEQ. ID No. 6 after guanidination.

It has been shown that photodissociation with 157 nm light yields abundant high-energy fragments that are strikingly different from those low-energy fragments generated with post-source decay. See e.g., Cui, W.; Thompson, M. S.; Reilly, J. P. J. Am. Soc. Mass Spectrom. 2005, 16, 1384-1398; Zhang, L.; Reilly, J. P. Anal. Chem. 2009, In press. Referring now to FIG. 1, fragments produced by these two techniques are compared. FIG. 1 displays a typical pair of photodissociation and PSD spectra. FIG. 1(A) is the PSD spectrum of guanidinated tryptic peptide MFLSFPTTK* (SEQ ID No. 6) which shows the spectrum is dominated by y-type ions. Ions that have lost ammonia are labeled with an asterisk (*). The photodissociation spectrum of the same peptide is displayed in FIG. 1(B). In addition to abundant high-energy x-, v- and w-type photofragments, most of the PSD fragments are also observed. This is because PSD fragments are not separated from precursor ions by the timed ion gate in the tandem-TOF mass spectrometer. Some of these fragments ($y_1$, $a_2$, $b_2$ and $b_3$) are further enhanced during photodissociation. Post-source decay spectra can be used to identify peaks in a photodissociation spectrum that are not x-, v- and w-type ions. When desired, PSD peaks can be removed from photodissociation spectra. Direct subtraction of spectra does not accomplish this since peaks in the two spectra differ in intensity. In this example, by magnifying the PSD spectrum in FIG. 1(A) by 5.0 times, subtracting it from the photodissociation spectrum in FIG. 1(B), and not plotting negative peaks, the result shown in FIG. 1(C) is obtained. It is evident that the photodissociation spectrum by itself contains primarily x-, v- and w-type ions that are complementary to the b- and y-type fragments in the PSD spectrum. Since y-type ions are always 25.98 Da lighter than the corresponding x-type ions, x/y ion pairs can easily be identified by comparison of PSD and photodissociation spectra. The observed y-type ions can sometimes be used to identify complementary b-type ions since the sum of their masses equals M+1 Da where M is the precursor mass.

In addition to identifying x-type ions, y-type ions are used to assign amino acids when the corresponding x-type ions are missing. As noted above, $y_1$ ions identify peptide C-terminal residues since they tend to be abundant in spectra recorded with the ABI 4700 MALDI TOF-TOF mass spectrometer[38]. As a result, peptide C-terminal residues can still be unambiguously identified even when the $x_1$ ions are missing. y-type ions are very important for identifying proline residues. As demonstrated in previous work, x-type ions terminated by proline are not observed at all in photodissociation spectra; instead Y-type ions at proline are always abundant[38]. For example in FIG. 1C, an intense $Y_4$ ion appears while the $x_4$ ion is missing. Fortunately in most PSD spectra, y-type ions terminated by proline are abundant because of preferential cleavage of Xxx-Pro bonds[24]. Since the y-type ions are always 2 Da heavier than the corresponding Y-ions, one helps to confirm the other. Observation of such ion pairs along with the absence of corresponding x-type ions points to proline residues. y-type ions are not typically formed at the C-terminal side of proline because Pro-Xxx bonds are not normally cleaved upon low-energy vibrational excitation[24]. For example in FIG. 1(A), the $y_3$ ion is missing. This information also helps to confirm a proline assignment. The combination of two sets of sequence ions reduces the risk of incomplete sequence identifications when one of the sequence ions is low in intensity and is not detected by the peak picking software. This is rather important for x-type ions in the low- or high-mass region that often exhibit low intensities[38]. A good example is the $x_2$ ion FIG. 1(C). If it were not recognized, the de novo sequencing algorithm would still be able to identify the amino acid by using the $y_2$ ion in the PSD spectrum.

Error Checking using v-, w-, and y-type Ions. In addition to x-type ions, photodissociation spectra (i.e. FIG. 1(C)) also contain many v- and w-type ions that result from amino acid side chain fragmentation. Since these fragments do not appear in low-energy PSD spectra (i.e. FIG. 1(A)), they can easily be recognized by comparison of the two sets of data. Side chain losses are widely observed in 157 nm photofragmentation spectra. Since the observed fragments correlate with residue side chain structures, they provide information about amino acid identities that complements the x- and y-ion mass differential data discussed above. The production of v- or w-type fragments is residue-dependent. In FIG. 1(C) for example, abundant $v_5$ and $v_8$ ions are observed at phenylalanine while $w_5$ and $w_6$ are formed at serine and leucine, respectively. Based on more than 200 photodissociation spectra obtained previously (See, Thompson, M. S.; Cui, W.; Reilly, J. P. Angew. Chem. Int. Ed. 2004, 43, 4791-4794; Cui et al.; Zhang and Reilly, herein) and in this experiment, the dependence of v- and w-type ions on amino acids is summarized in Table 2.

TABLE 2

Observation of v- and w-type ions at different amino acids

| Amino acids | Monoisotopic masses (Da) | Mass spacings from x- ion (Da) | |
|---|---|---|---|
| | | v-type ion | w-type ion |
| Glycine (G) | 57.02 | — | — |
| Alanine (A) | 71.04 | 42.01 | — |
| Proline (P) | 97.05 | — | 69.02 |
| Valine (V) | 99.07 | 70.04 | 57.02 |
| Leucine (L) | 113.08 | — | 85.05 |
| Isoleucine (I) | 113.08 | 84.06 | 71.04 |
| Glutamine (Q) | 128.06 | — | 100.03 |
| Glutamic acid (E) | 129.04 | — | 101.01 |
| Serine (S) | 87.03 | — | 59.00 |
| Threonine (T) | 101.05 | 72.02 | 59.00 |
| Phenylalanine (F) | 147.07 | 118.04 | — |
| Tyrosine (Y) | 163.06 | 134.04 | — |
| Tryptophan (W) | 186.08 | 157.05 | — |
| Histidine (H) | 137.06 | 108.03 | — |
| Aspartic acid (D) | 115.03 | — | 87.00 |
| Asparagine (N) | 114.04 | — | 86.01 |
| Methionine (M) | 131.04 | — | 103.01 |
| Cysteine (C) | 103.01 | — | 74.98 |
| Lysine (K) | 128.09 | — | 100.06 |
| Arginine (R) | 156.10 | — | — |

For aromatic amino acids, only v-type ions are abundantly formed (Scheme 1A); w-type ions are not produced because cleavage of side chain $C_\beta$—$C_\gamma$ bonds at aromatic residues is thermodynamically disfavored. For most non-aromatic amino acids except valine, threonine and isoleucine, only w-type ions appear in photodissociation peak lists while the v-type ions are usually low in intensity. This is because these non-aromatic amino acids do not contain any substituent on the β-carbon. Formation of v-type ions (Scheme 1A) is disfavored since it involves releasing an unstable secondary radical. In addition, these v-type ions overlap with the $^{13}C$ component of the corresponding w-type ions. As a result, the v-type ions of most non-aromatic amino acids are not identified by the ABI Data Explorer peak picking software and are not exported in photodissociation peak lists. In contrast, isoleucine, threonine and valine yield v- and w-type ions that are spaced by 13.02 Da. Production of v-type ions at these three residues is enhanced because it involves the release of a stable tertiary radical. The observed side chain fragments and their mass spacings from corresponding x-type ions are summarized in Table 2.

Scheme 1:

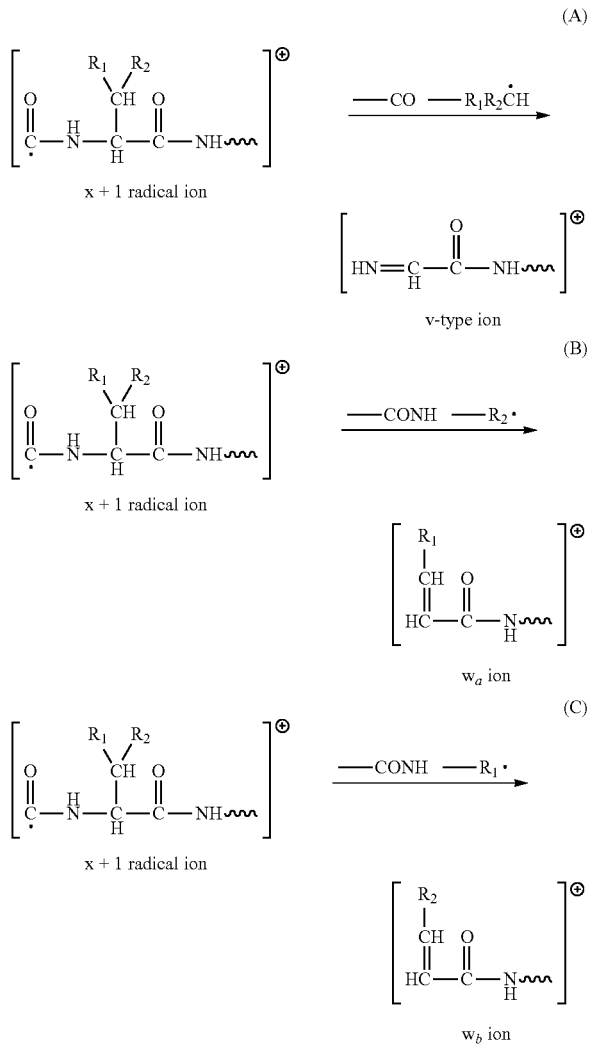

Note that isoleucine and threonine have two different β-substitutents on their side chains and thus both can yield two different w-type ions (Schemes 1B and 1C). However, only one of these is usually observed in photodissociation spectra. At isoleucine, loss of the ethyl group occurs while loss of the hydroxyl group is favored at threonine. The mass spacings of these two w-type ions from the corresponding x-type ions are listed in Table 2.

Observation of y-, w-, and v-type ions adds different degrees of confidence to amino acid assignments. y-type ions are the major fragments in PSD spectra and they are always 25.98 Da lighter than the corresponding x-type ions. Detection of these ions in PSD spectra confirms most x-type ion assignments. As a result, amino acid assignments based on x/y ion pairs are given a confidence score of 1.0. It is noteworthy that y-type ions observed only in photodissociation spectra are not used to confirm the x-type ion assignments because photodissociation spectra contain many fragments and there is a non-negligible probability that some of these may happen to match the mass of a y-type ion. Nevertheless, observation of these y-type ions adds some confidence to amino acid assignments. Likewise, observation of v- and w-type ions does not confirm x-type ion assignments even though their mass spacings from the corresponding x-type ions are unique to each amino acid. This is because multiple amino acids lead to v- and w-type ions that have the same mass. For example, w-type ions terminated by all non-aromatic amino acids except valine, threonine isoleucine are isobaric. Likewise, since v-type ions are formed by loss of a complete side chain, their masses are independent of the N-terminal residue. Nevertheless, observation of these ions adds some confidence to amino acid assignments that are not based on x/y ion pairs. In this algorithm, amino acid assignments based on x- or y-ions are checked by observation of all sequence ions including x-, y-, v-, and w-type fragments. Since the production of v- and w-type ions is residue-dependent, the number of the expected sequence ions varies with amino acid. As a result, the ratio of the number of observed sequence ions over the expected number is arbitrarily used to define the confidence level of amino acid assignments based on x- or y-ions. Immonium ions are abundantly observed in photodissociation spectra, and they could provide additional constraints on the presence of some amino acids. However, they are not included in the present algorithm.

The confidence of a proposed sequence is evaluated by the average score associated with all amino acid assignments. The overall scores not only reflect the credibility of a sequence, but are also useful to rank sequence candidates when necessary. In addition, the algorithm displays all of the observed sequence-related ions for each amino acid assignment. These details facilitate manual checking of sequencing results and they should be useful in future statistical evaluations of the residue-dependence of photofragmentation.

De Novo Sequencing.

In order to demonstrate how the algorithm derives sequences and checks for errors, the step by step process as applied to the spectra in FIG. 1 will be considered. First, peak lists from FIG. 1(A) and FIG. 1(B) are compared, which identifies five x/y ion pairs: $x_1/y_1$, $x_2/y_2$, $x_5/y_5$, $x_6/y_6$ and $x_7/y_7$. The mass differentials between the x-type ions identify four amino acids and two gaps: [278.18 Da]LS [345.18 Da]TK*, where the asterisk (*) represents guanidinated lysine. Second, the algorithm tries to bridge the 345.18 Da gap by looking for possible x-type ions between the $x_2$ (316.16 Da) and $x_5$ (661.34 Da). To identify the $x_3$ fragment, the algorithm searches for peaks that are within 186.5 Da of $x_2$. The $x_3$ ion in FIG. 1(B) is considered to be a candidate since its spacing from the $x_2$ ion matches that of threonine (101.05 Da). This assignment is further confirmed by observation of the $v_3$ and $w_3$ ions at masses consistent with the threonine residue. No other $x_3$ ion candidates are found. The algorithm subsequently looks for possible $x_4$ ions based on mass spacings from $x_3$, but none of the peaks in the spectrum matches. It then looks for possible $y_4$ ions based on mass spacings from the calculated $y_3$ ion at 391.26 Da ($x_3$−25.98 Da). The $y_4$ ion is found to be a candidate since its spacing from the putative $y_3$ ion matches that of proline (99.05 Da). This assignment is further confirmed by observation of a 2 Da lighter $Y_4$ ion and the absence of $y_3$ and $x_4$ ions from the spectrum. The algorithm then calculates the value that the $x_4$ ion should be ($y_4$+25.98 or 514.25 Da) and considers if this is consistent with the assignment of the following amino acid. The fifth residue is then determined by the mass spacing between $x_5$ and the calculated $x_4$ mass. The mass differential of 147.09 Da suggests that it can be either a phenylalanine or an oxidized methionine. An abundant $v_5$ ion at a mass appropriate for phenylalanine supports this assignment. (Differentiating these two amino acids is further discussed in the following section.) The gap of 345.18 Da is thus interpreted as FPT. Likewise, detection of an $x_8$ ion at 1008.52 Da suggests that the eighth residue from the peptide C-terminus is either a phenylalanine or an oxidized methionine since it is shifted from the $x_7$ ion by 147.08 Da. An abundant $v_8$ ion at a mass appropriate for phenylalanine supports this assignment. Since the residual mass of the N-terminal gap is 131.10 Da, the last residue of this sequence is assigned as methionine. The 278.18 Da gap is therefore assigned as MF. In summary, the entire peptide sequence is interpreted as SEQ ID NO. 6 (MFLSFPTTK*).

After determining a candidate sequence, the algorithm evaluates the confidence scores of all amino acid assignments. In the previous example, the four residues identified with x/y ion pairs are assigned confidences of 1.0 as indicated above while other assignments are evaluated based on the occurrence of x-, v-, w- and y-type fragments in the photodissociation spectrum. For example, at the eighth residue from the peptide C-terminus, two sequence ions ($x_8$ and $v_8$) are observed. Since three sequence ions are actually expected for phenylalanine ($x_8$, $y_8$, and $v_8$), the confidence score of this assignment is assigned as 0.67. By averaging the confidence scores of all amino acid assignments, the overall confidence score of the sequence is 0.906. These confidence scores are used to rank sequence candidates when multiple sequences are derived from photodissociation data.

Analysis of Tryptic Peptides from Model Proteins.

Tryptic peptides are guanidinated prior to photodissociation for three reasons. First, lysine-terminated peptides yield higher precursor ion intensities since guanidination increases their gas-phase basicity. Second, guanidinated peptides yield more abundant high-energy photofragments than unmodified lysine-terminated peptides because the guanidino group sequesters the charging proton. Third, as noted before, guanidination makes it easier to differentiate lysine and glutamine. Lysine (128.095 u) and glutamine (128.059 Da) cannot be distinguished by low-resolution mass spectrometers, but guanidination converts lysine to homoarginine (170.13 Da). Although homoarginine has a mass close to several amino acid combinations (i.e. AV, IG and LG), this rarely induces ambiguities during sequence interpretation because for tryptic peptides it is primarily located at peptide C-termini.

To evaluate the accuracy of this sequencing approach, peptides from human hemoglobin, horse myoglobin, horse cytochrome C and bovine ubiquitin were fragmented by photodissociation and PSD, and then sequenced. Results are summarized in Table 3.

TABLE 3

De novo sequencing of tryptic peptides from four model proteins

| SEQ ID NO. | Actual sequence | Interpreted sequence | Total Residues | Correct Assignments | Incorrect Assignments | Unassigned Residues |
|---|---|---|---|---|---|---|
| hemoglobin, human ||||||||
| 1 | EFTPPVQAAYQK | EFTPPVQAAYQK | 12 | 12 | 0 | 0 |
| 2 | TYFPHFDLSHGSAQVK | [264.098]FPHFDLSHGSA[227.29]K | 16 | 12 | 0 | 4 |
| 3 | FFESFGDLSTPDAVMGNPK | [423.105]SFGDLSTPDAVMGNPK | 19 | 16 | 0 | 3 |
| 4 | VLGAFSDGLAHLDNLK | V[I\|L]GAFSDGLAHLDN[I\|L]K | 16 | 16 | 0 | 0 |
| 5 | VGAHAGEYGAEALER | VGAHAGEYGAEALER | 15 | 15 | 0 | 0 |
| 6 | MFLSFPTTK | MFLSFPTTK | 9 | 9 | 0 | 0 |
| 7 | LLVVYPWTQR | [I\|L]LVVYPWTQR | 10 | 10 | 0 | 0 |
| 8 | VHLTPEEK | VHLTPEEK | 8 | 8 | 0 | 0 |
| 9 | SAVTALWGK | SAVTALWGK | 9 | 9 | 0 | 0 |
| 10 | VNVDEVGGEALGR | VNVDEVGGEALGR | 13 | 13 | 0 | 0 |
| myoglobin, horse ||||||||
| 11 | HGTVVLTALGGILK | HGTVVLTALGGILK | 14 | 14 | 0 | 0 |
| 12 | HGTVVLTALGGILKK | HGTVVLTALGGIL[170.22]K | 15 | 14 | 0 | 1 |
| 13 | LFTGHPETLEK | [I\|L]FTGHPETLEK | 11 | 11 | 0 | 0 |
| 14 | HPGDFGADAQGAMTK | HPGDFGADAQGAMTK | 15 | 15 | 0 | 0 |
| 15 | VEADIAGHGQEVLIR | VEADIAGHGQEVLLR | 15 | 14 | 1 | 0 |
| 16 | YLEFISDAIIHVLHSK | [405.145]FISDAIIHVLHSK | 16 | 13 | 0 | 3 |
| 17 | ALELFR | [184.184]ELFR | 6 | 4 | 0 | 2 |
| cytochrome c, horse ||||||||
| 19 | TGQAPGFTYTDANK | TGQAPGFTYTDANK | 14 | 14 | 0 | 0 |
| 20 | TGPNLHGLFGR | TGPNLHGLFGR | 11 | 11 | 0 | 0 |
| 22 | TGPNLHGLF | TGPN[612.36] | 9 | 4 | 0 | 5 |
| 23 | MIFAGIK | MIFAGIK | 7 | 7 | 0 | 0 |
| 24 | EDLIAYLK | EDLIAYLK | 8 | 8 | 0 | 0 |
| 25 | KYIPGTK | [170.151]YIPGTK | 7 | 6 | 0 | 1 |
| 26 | EETLMEYLENPK | EETDEEYLENPK | 12 | 10 | 2 | 0 |
| ubiquitin, bovine ||||||||
| 27 | TLSDYNIQK | TLSDYNIQK | 9 | 9 | 0 | 0 |
| 28 | ESTLHLVLR | ESTLHLVLR | 9 | 9 | 0 | 0 |
| 29 | EGIPPDQQR | EGIPPDQQR | 9 | 9 | 0 | 0 |
| 31 | IQDKEGIPPDQQR | [526.263]EGIP[468.31]R | 13 | 5 | 0 | 8 |
| 32 | M*QIFVK [a] | [M*\|F]QIFVK | 6 | 6 | 0 | 0 |

TABLE 3-continued

De novo sequencing of tryptic peptides from four model proteins

| SEQ ID NO. | Actual sequence | Interpreted sequence | Total Residues | Correct Assignments | Incorrect Assignments | Unassigned Residues |
|---|---|---|---|---|---|---|
| 32 | MQIFVK | MQIFVK | 6 | 6 | 0 | 0 |
| 33 | TITLEVEPSDTIENVK | [315.145]LEVEPSDTIENVK | 16 | 13 | 0 | 3 |
| | Total residues | | 355 | 322 | 3 | 30 |
| | Percentage | | | 90.7 | 0.8 | 8.5 |

Asterisk symbol (*) denotes oxidation of methionine. [X|Y] denotes a residue that can be either X or Y residue. Incorrect amino acid assignments are underscored.

Figure 2A:
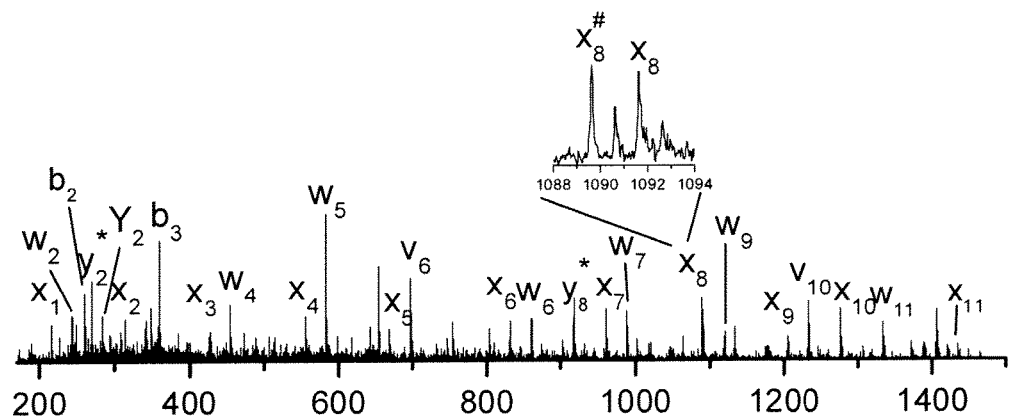
FIG. 2(A) shows photodissociation spectrum of a peptide, SEQ. ID NO. 26 (EETLMEYLENPK) after guanidination.
Figure 2B:
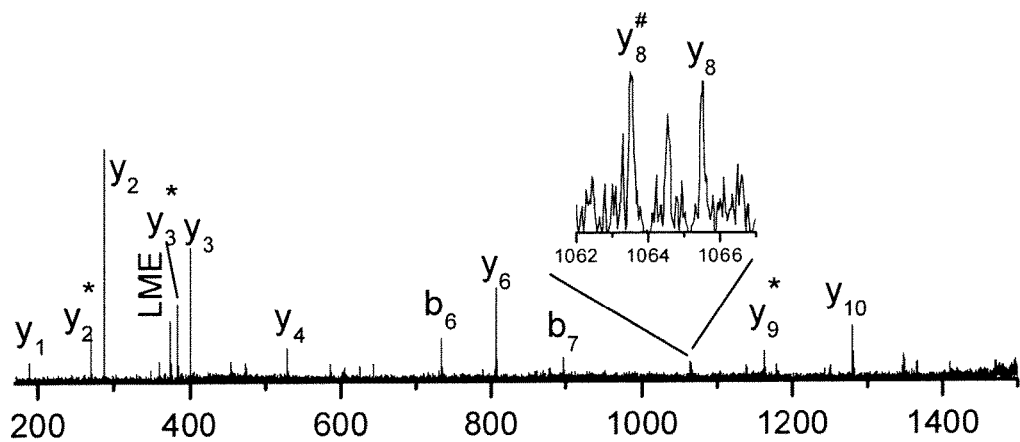
FIG. 2(B) shows post-source decay spectrum of SEQ. ID NO. 26 after guanidination.

Referring now to Table 3, 29 out of 31 yielded sequences with 5 or more residues. Comparison with the protein database showed that 322 out of 355 (90.7%) amino acids were correctly identified. Of the remaining 33 amino acids, 28 were not identified at all and there were 3 incorrect amino acid assignments. 2 of the incorrect assignments appeared in peptide EETLMEYLENPK (SEQ ID NO. 26) from horse cytochrome C, in which LM was incorrectly interpreted as DE as shown in Table 3. After the peptide was identified by referring to the protein sequence, its photodissociation spectrum was further interpreted. PSD fragments were removed and the spectrum replotted as displayed in FIG. 2(A). Similar to FIG. 1(C), it is dominated by x-, v- and w-type ions. During de novo sequencing, two candidate x8 ions were found (labeled as $x_8\#$ and $x_8$) that are terminated by glutamate and methionine, respectively. Remarkably, both of the corresponding y-type ions ($y_8\#$ and $y_8$) also appeared in the PSD spectrum (FIG. 2B), and this led to the incorrect assignment.

Figure 3:
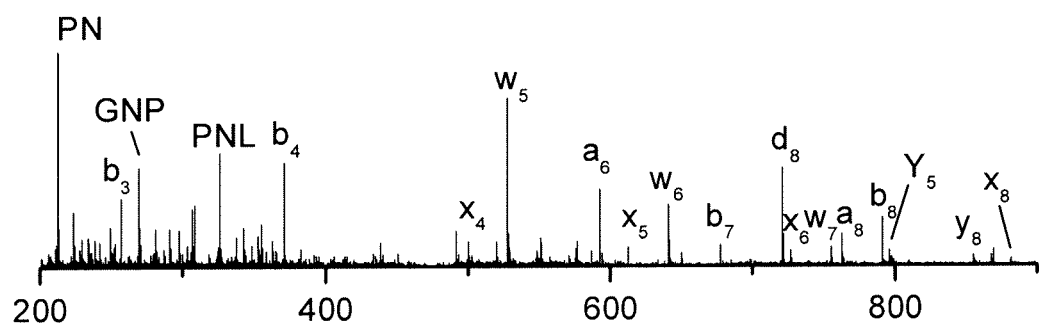
FIG. 3 shows photodissociation spectrum of a peptide, SEQ. ID No. 22 (TGPNLHGLF) after removal of post-source decay fragments.

Only four residues of peptide TGPNLHGLF (SEQ ID NO. 22) from horse cytochrome C, were properly sequenced, but it still could be identified by referring to the protein sequence. This peptide was generated as a side product of the chymotryptic digestion of larger tryptic peptides. As seen in FIG. 3, the sequencing gap is induced because $x_1$-$x_3$ are not detected. This results because the most basic residue in this sequence, histidine, preferentially binds the ionizing proton and thus cleavage of backbone bonds to its C-terminal side does not yield x-type ions. Instead, N-terminal $a_6$, $b_7$, $a_8$, and $b_8$ ions are produced. However, they are not used to derive sequences by the present algorithm. To enable more residues from non-tryptic peptides to identified, the sequencing algorithm should interpret both N- and C-terminal fragments. This will also facilitate identification of tryptic peptides with missed cleavages that lead to abundant N-terminal fragments.

Compared with conventional de novo analyses of low-energy CID or TOF-TOF CID data, the present method generates rather few incorrect amino acid assignments. This is directly attributable to the use of constraint ions to check each amino acid assignment. Tentative amino acid assignments with low confidence are not labeled with their identities, but by mass gaps. In contrast, most conventional algorithms generate complete peptide sequences that contain multiple incorrect amino acid assignments. Without reference to a protein database, these false assignments are difficult to recognize. This poses a challenge for protein identification using sequence homology searches in which multiple amino acid errors would need to be allowed, thereby increasing the search times and numbers of false identifications. To avoid incorrect amino acid assignments, Pevzner and coworkers proposed an alternative "spectral profile" approach to represent de novo sequencing results (See, Kim, S.; Bandeira, N.; Pevzner, P. A. *Mol. Cell. Proteomics* 2009, 8, 1391-1400). In their method, only highly confident amino acid assignments are identified; others are represented by mass gaps. As exemplified by some of the above discussion, this strategy is adopted by the present sequencing approach. A second advantage of photodissociation/de novo sequencing method is the high sequence coverage that is achieved. With this four protein sample set, over 90% sequence coverage was obtained. Conventional methods typically generate less than 66% sequence coverage for tryptic peptides from standard protein digests according to Bringans and coworkers' assessment of three commercial de novo sequencing software packages (See, Bringans, S.; Kendrick, T. S.; Lui, J.; Lipscombe, R. *Rapid Commun. Mass Spectrom.* 2008, 22, 3450-3454). In their experiment, lower peptide quantities (50 fmol) were analyzed by an ABI 4800 TOF-TOF mass spectrometer that is generally considered to be 10 times as sensitive as the ABI 4700 TOF-TOF mass spectrometer employed in this study. Thus, although the comparison is not exactly rigorous, the two experiments should be comparable.

It is noteworthy that the N-terminal two amino acids in peptide ALELFR (SEQ ID NO. 17) from horse myoglobin were not identified. This is because the $x_5$ ion was not detected in the photodissociation spectrum obtained by the ABI 4700 TOF-TOF mass spectrometer due to the instrument's low sensitivity in the high mass region. However, this fragment ion was an intense feature in previous photodissociation TOF-TOF spectra recorded with a homebuilt instrument (See, Thompson et al. herein). This suggests that additional information should be extractable with improved instrument tuning, particularly in the low- and high-mass regions.

Differentiating Leucine and Isoleucine.

Leucine and isoleucine can be distinguished based on their unique side chain fragments produced by 157 nm photodissociation as shown in Table 1. Leucine primarily leads to w-type ions that are 85.05 Da lighter than the corresponding x-type ions. Isoleucine yields both v- and w-type ions that are 84.06 and 71.04 Da lighter than the corresponding x-type ions, respectively. Since the two w-type ions are spaced by 14.01 Da, they have been used to distinguish the two isomers in high-energy fragmentation experiments.

The present de novo approach uses both w- and v-type ions to distinguish leucine and isoleucine as follows. The algorithm first looks for the w-type ions that are either 71.04 or 85.05 Da lighter than the x-type ion. When only the former peak is observed, the amino acid is assigned as isoleucine; the corresponding v-type ion that is 84.06 Da lighter than the x-type ion is then sought to confirm this assignment. When only the latter peak is detected, leucine is identified.

Results for distinguishing leucine and isoleucine in the four model proteins are summarized in Table 4.

TABLE 4

Differentiation of leucine and isoleucine in four model proteins

| Proteins | Observed Xle | Identified Xle | Differentiated Xle | Incorrect Assignments |
|---|---|---|---|---|
| hemoglobin | 12 | 12 | 9 | 0 |
| myoglobin | 20 | 18 | 16 | 1 |
| cytochrome C | 12 | 9 | 9 | 0 |
| ubiquitin | 13 | 11 | 11 | 0 |
| Total residues | 57 | 50 | 45 | 1 |
| Percentage of distinguishing Xle (%) | | | 90.0 | 2.0 |

Xle denotes an amino acid that can be either leucine or isoleucine.

In total, 57 leucine or isoleucine (Xle) residues appeared in the 31 observed peptides. 45 of these were correctly differentiated, four were identified as one or the other of these and seven were not identified because the corresponding x-type ions were not detected in photodissociation spectra. One isoleucine, in peptide VEADIAGHGQEVLIR (SEQ ID NO. 15), was mistakenly assigned as leucine. Two of the four 4 indistinguishable residues were located at peptide N-termini that did not yield side chain fragments while the other two were near peptide termini where side chain fragments are often not detected as noted above. The error in the isoleucine assignment resulted because neither $W_2$ or $v_2$ were observed in the photodissociation spectrum due to low sensitivity in the low-mass region. However, in this particular spectrum, an abundant $b_2$ ion at 229.14 Da was misassigned as a $W_2$ ion terminated by leucine (expected at 229.13 Da). Thus 98.0% of the identified leucines and isoleucines were correctly distinguished, but fortuitous errors such as this one may be difficult to completely eliminate.

Differentiating Phenylalanine and Oxidized Methionine.

Phenylalanine (147.068 Da) and oxidized methionine (147.040 Da) are a challenge to distinguish in a MALDI TOF-TOF instrument. However, they can be easily identified by their side chain fragments in photodissociation experiments. As displayed in Table 2, methionine primarily leads to w-type ions that are shifted from the corresponding x-type ions by 103.01 Da. Oxidized methionine yields w-type ions that are 119.00 Da lighter than the corresponding x-type ions. In contrast, phenylalanine leads to abundant v-type ions that are 118.04 Da lighter than the x-type ion. Since these two side chain fragments differ by 0.96 Da, they can easily distinguish phenylalanine and oxidized methionine.

As shown in Table 3, all phenylalanine residues were correctly identified based on observation of v-type ions. This is consistent with the fact that v-type ions terminated by aromatic amino acids are usually abundant in photodissociation spectra. Only one oxidized methionine residue was in this sample set in peptide M*QIFVK (SEQ ID NO. 32) from bovine ubiquitin. Because it resides at the peptide N-terminus where side chain fragments are often not generated, it was not possible to distinguish between the two assignments. However, the native, unoxidized form of this peptide was also in the sample set and in this case the methionine was identified, as noted in Table 3.

Protein Identification by Homology Searches.

The ability to identify proteins using peptide de novo sequencing was investigated by matching the sequencing results against a protein sequence database. All of the interpreted sequences in Table 3 were submitted to the MS-Homology program to match against the SwissProt. 2008 Jun. 10 database containing 389046 proteins. 26 of the 31 sequences identified a unique peptide in the database. Since these peptides can be generated from protein homologues in different organisms, each of them typically matched multiple proteins in the database. When the organism under study was further used to constrain the matching results, each of the 26 sequences matched a unique protein.

The remaining five sequences did not lead to identification of a unique protein for two reasons. In three cases, [184.184]ELFR (SEQ ID NO. 18) from horse myoglogbin, TGPN (SEQ ID NO. 21) from horse cytochrome C and EGIP (SEQ ID NO. 30) from bovine ubiquitin, the short sequences matched numerous peptides from non-homologous proteins in the database. (Mass gaps in the latter two sequences were not included in the search because they were too large to be accepted by the searching algorithm.) To address these ambiguities, another search was performed with a smaller database that contained only equine or bovine proteins. The first two sequences each matched a unique equine peptide that translated into a correct protein identification, the third matched several peptides from different bovine proteins. Although the non-tryptic peptide TGPNLHGLF (SEQ ID NO. 22) yielded a four-residue sequence that led to an ambiguous protein identification, all residues of the corresponding tryptic peptide TGPNLHGLFGR (SEQ ID NO. 20) were assigned and this translated to a unique protein identification. A second reason for unsuccessful protein identification is that two sequences, EET DEEYLENPK (incorrect amino acid assignment of SEQ ID NO. 26) and VEADIAGHGQEVLLR (incorrect amino acid assignment of SEQ ID NO. 15) did not match with any peptide in the SwissProt database because of the one or two incorrect amino acid assignments noted in Table 3. However, a sequence homology search allowing up to two errors successfully matched unique proteins in the database.

Assessing the Scoring Approach.

To more thoroughly evaluate the present sequencing approach, the 23 proteins listed in Table 1 were each digested separately. The resulting tryptic peptides from each protein were guanidinated and then purified by microextraction tips. Each tryptic digest was deposited to create one or two MALDI spots and each spot contained 2.5 pmol of materials. A total of 266 tryptic peptides were isolated, fragmented by photodissociation and PSD, and then sequenced.

167 of the 266 peptides whose precursor ions were fragmented led to sequences with 5 or more residues. This corresponds to 62.8% of the photodissociation spectra. Of the 167 peptides, only 5 sequences contain one or two incorrect amino acid assignments, corresponding to a false identification rate of 3.0%. The other 99 peptide ions that were photofragmented yielded limited sequence information for two principal reasons. First, many peptides contained more than one arginine or homoarginine due to a missed tryptic cleavage and these typically led to incomplete x-type ion series[38]. For example, peptide IQDKEGIPPDQQR (SEQ ID NO. 31) from bovine ubiquitin yielded a sequence of only four consecutive amino acids as noted in Table 3. A second problem for sequencing was that some peptide precursor ions were low in intensity. This resulted because ten precursor ions were isolated for fragmentation from each spot and the last few of these often had low abundances since the spot was significantly depleted after thousands of MALDI shots.

The top ranked sequences for the 167 peptides (which were not always the same as the longest sequences determined), were used in homology searches against a database in order to assess their accuracy. 163 (97.6%) of these sequences contained all correct amino acid assignments. 68 (or 40.7%) of them were shorter than the longest sequences by one or more amino acids. This resulted because long sequences usually had fewer confirmations than short sequences, leading to lower scores. However, the top ranked sequences were still able to identify unique proteins since they were accurate and usually contained five and more residues. In addition, gaps in these sequences could be used as additional constraints during sequence matching as pointed out by Pevzner and coworkers.

Completeness of the Derived Sequences.

Although the present approach yields high peptide sequence coverage, it still leads to numerous gapped sequences as shown in Table 3. Of the 167 successfully sequenced peptides, 96 (or 57.6%) yielded complete sequences. Of the remaining 71 peptides, 62 had an N-terminal mass gap and 30 peptides had a C-terminal mass gap. A total of 22 peptides had both N- and C-terminal gaps. However, only 1 sequence contained a gap in the middle. This gap distribution is consistent with the mass spectrometer's sensitivity, which is highest in the middle of the mass range and drops towards each end. Accordingly, most x-type ions in the middle mass region are detected while some of them are missing in the low- or high-mass regions. Although gaps do not reveal any sequence information, they are still useful to protein identification by providing additional constraints as noted above.

In illustrative embodiments, the de novo sequencing algorithm described herein interprets photodissociation spectra resulting from photodissociation with a 157 nm laser. However, one of ordinary skill in the art will appreciate that other high-energy photodissociation sources may be similarly used. In one embodiment, a 193 nm laser may be used. In another embodiment, any available, or later-developed, laser providing sufficient levels of radiation in the range of from about 100 nm to about 200 nm may be used, so long as the resulting photodissociation spectra is of sufficient quality. One of ordinary skill in the art will appreciate that a photodissociation spectrum of sufficient quality is characterized as exhibiting sufficient fragmentation across the peptide. Sufficient fragmentation across the peptide is characterized as fragmentation which is at least equivalent to that fragmentation shown in FIG. 1(B).

By combining photodissociation and PSD data, this algorithm identifies x/y ion pairs and derives peptide sequences. Observation of y-, w- and v-type ions provides additional constraints to amino acid assignments. In the analysis of 31 tryptic peptides from 4 model proteins, 322 (or 90.7%) of the amino acids are correctly identified, which is excellent by comparison with conventional de novo methods that interpret low-energy fragmentation data. Of the remaining 33 amino acids, 30 of them are not identified at all and there are three mistakes. The present de novo sequencing approach also allows leucine and isoleucine to be differentiated using side chain v- and w-type fragments. 45 of the 50 identified leucine and isoleucine residues in the data set are successfully distinguished. Of the remaining five residues, four are not distinguished because of undetected v- and w-type ions and there is only one mistake. These derived sequences are shown to be capable of identifying proteins from a large database using homology searches. In the analysis of a larger data set containing 266 tryptic peptides, 167 (or 62.8%) of them lead to sequences with five or more identified amino acids. Only five sequences contained one or two false amino acid assignments, which is about 3.0% of the total identified sequences.

What is claimed is:

1. A method for de novo sequencing of a peptide or a protein by fragmentation and mass spectrometry comprising:
  low-energy fragmentation of the peptide or protein into first product ions selected from the group consisting of b- and y-type ions and obtaining first mass spectral data of the first product ions;
  high-energy fragmentation of the same peptide or the same protein into second product ions selected from the group consisting of a-, b-, c-, d-, v-, w-, x-, and y-type ions and obtaining second mass spectral data of the second product ions;
  identifying fragment ion types by adding and subtracting masses of the second product ions to establish the presence of related peaks associated with predetermined mass spacings of ion types and pairing a first mass from the first product ions and a second mass from the second product ions;
  and de novo sequencing the peptide or protein, wherein de novo sequencing comprises subtracting masses of the second product ions after identifying the fragment ion types to establish the presence of related peaks associated with amino acid molecular weights.

2. The method of claim 1 wherein low-energy fragmentation comprises post-source decay (PSD) following one of matrix assisted laser desorption ionization (MALDI) and collision-induced dissociation (CID) following electrospray ionization (ESI).

3. The method of claim 1 wherein high-energy fragmentation comprises photodissociation.

4. The method of claim 3 wherein photodissociation comprises vacuum ultraviolet photodissociation.

5. The method of claim 1 wherein de novo sequencing comprises exploiting a number of similarities arising from the presence of related peaks associated with predetermined mass differences and predetermined mass sums in the second mass spectral data.

6. The method of claim 5 wherein comprising adding a first value from the second mass spectral data to a second value from the second mass spectral data to obtain a predetermined mass sum, the predetermined mass sum being one of the sum of:
  (i) an $a_n$ fragment and an $x_{N-n}$ fragment;
  (ii) a $b_n$ fragment and an $x_{N-n}$ fragment;
  (iii) an $a_n$ fragment and a $v_{N-n+1}$ fragment; and
  (iv) a $b_n$ fragment and a $v_{N-n+1}$ fragment, where n is the number of residues from a C terminus of the peptide or protein and N is the number of residues in the peptide or protein.

7. The method of claim 6 wherein the predetermined mass sum is one of M−1.01 Da, M+26.99 Da, M+28.02 Da, M+56.01 Da, M+27.02 Da, M+41.02 Da, M+55.02 Da, and M+69.02, where M is a measured peptide ion mass.

8. The method of claim 5 comprising subtracting a first value from the second mass spectral data from a second value from the second mass spectral data to obtain a predetermined mass difference, the predetermined mass difference being one of the difference between:
  (i) an $x_n$ fragment and a $y_n$ fragment;
  (ii) a $v_{n+1}$ fragment and an $x_n$ fragment;
  (iii) a $w_{n+1}$ fragment and an $x_n$ fragment;
  (iv) a $v_{n+1}$ fragment and a $y_n$ fragment; and
  (v) a $w_{n+1}$ fragment and a $y_n$ fragment,
where n is the number of residues from a C terminus of the peptide or protein.

9. The method of claim 8 wherein the predetermined mass difference is 25.98 Da.

10. The method of claim 8 wherein the predetermined mass difference is one of 29.03 Da, 28.03 Da, 42.04 Da, 55.01 Da, 54.01 Da, or 68.02 Da.

11. The method of claim 1 further comprising guanidinating a peptide.

12. The method of claim 1 wherein de novo sequencing of a peptide or a protein by fragmentation and mass spectrometry comprises de novo sequencing of a tryptic peptide from a digestion of a protein.

13. The method of claim 1 further comprising assigning arginine as a C-terminal residue if 175.12 Da is in the second mass spectral data.

14. The method of claim 1 further comprising assigning guanidinated lysine as a C-terminal residue if 189.13 Da is in the second mass spectral data.

15. The method of claim 1 further comprising comparing an amino acid residue molecular weight to a difference between ion types from the second mass spectral data whether or not the ion types are in the first mass spectral data.

16. The method of claim 1 wherein the method for de novo sequencing is capable of differentiating leucine and isoleucine.

17. The method of claim 1 further comprising differentiating leucine and isoleucine.

* * * * *

SEQUENCE LISTING

```
<160> NUMBER OF SEQ ID NOS: 33

<210> SEQ ID NO 1
<211> LENGTH: 12
<212> TYPE: PRT
<213> ORGANISM: Homo sapiens

<400> SEQUENCE: 1

Glu Phe Thr Pro Pro Val Gln Ala Ala Tyr Gln Lys
1               5                   10

<210> SEQ ID NO 2
<211> LENGTH: 16
<212> TYPE: PRT
<213> ORGANISM: Homo sapiens

<400> SEQUENCE: 2

Thr Tyr Phe Pro His Phe Asp Leu Ser His Gly Ser Ala Gln Val Lys
1               5                   10                  15

<210> SEQ ID NO 3
<211> LENGTH: 19
<212> TYPE: PRT
<213> ORGANISM: Homo sapiens

<400> SEQUENCE: 3
```

```
Phe Phe Glu Ser Phe Gly Asp Leu Ser Thr Pro Asp Ala Val Met Gly
1               5                   10                  15

Asn Pro Lys
```

<210> SEQ ID NO 4
<211> LENGTH: 16
<212> TYPE: PRT
<213> ORGANISM: Homo sapiens

<400> SEQUENCE: 4

```
Val Leu Gly Ala Phe Ser Asp Gly Leu Ala His Leu Asp Asn Leu Lys
1               5                   10                  15
```

<210> SEQ ID NO 5
<211> LENGTH: 15
<212> TYPE: PRT
<213> ORGANISM: Homo sapiens

<400> SEQUENCE: 5

```
Val Gly Ala His Ala Gly Glu Tyr Gly Ala Glu Ala Leu Glu Arg
1               5                   10                  15
```

<210> SEQ ID NO 6
<211> LENGTH: 9
<212> TYPE: PRT
<213> ORGANISM: Homo sapiens

<400> SEQUENCE: 6

```
Met Phe Leu Ser Phe Pro Thr Thr Lys
1               5
```

<210> SEQ ID NO 7
<211> LENGTH: 10
<212> TYPE: PRT
<213> ORGANISM: Homo sapiens

<400> SEQUENCE: 7

```
Leu Leu Val Val Tyr Pro Trp Thr Gln Arg
1               5                   10
```

<210> SEQ ID NO 8
<211> LENGTH: 8
<212> TYPE: PRT
<213> ORGANISM: Homo sapiens

<400> SEQUENCE: 8

```
Val His Leu Thr Pro Glu Glu Lys
1               5
```

<210> SEQ ID NO 9
<211> LENGTH: 9
<212> TYPE: PRT
<213> ORGANISM: Homo sapiens

<400> SEQUENCE: 9

```
Ser Ala Val Thr Ala Leu Trp Gly Lys
1               5
```

<210> SEQ ID NO 10
<211> LENGTH: 13
<212> TYPE: PRT
<213> ORGANISM: Homo sapiens

<400> SEQUENCE: 10

Val Asn Val Asp Glu Val Gly Gly Glu Ala Leu Gly Arg
1               5                   10

<210> SEQ ID NO 11
<211> LENGTH: 14
<212> TYPE: PRT
<213> ORGANISM: Equus ferus

<400> SEQUENCE: 11

His Gly Thr Val Val Leu Thr Ala Leu Gly Gly Ile Leu Lys
1               5                   10

<210> SEQ ID NO 12
<211> LENGTH: 15
<212> TYPE: PRT
<213> ORGANISM: Equus ferus

<400> SEQUENCE: 12

His Gly Thr Val Val Leu Thr Ala Leu Gly Gly Ile Leu Lys Lys
1               5                   10                  15

<210> SEQ ID NO 13
<211> LENGTH: 11
<212> TYPE: PRT
<213> ORGANISM: Equus ferus

<400> SEQUENCE: 13

Leu Phe Thr Gly His Pro Glu Thr Leu Glu Lys
1               5                   10

<210> SEQ ID NO 14
<211> LENGTH: 15
<212> TYPE: PRT
<213> ORGANISM: Equus ferus

<400> SEQUENCE: 14

His Pro Gly Asp Phe Gly Ala Asp Ala Gln Gly Ala Met Thr Lys
1               5                   10                  15

<210> SEQ ID NO 15
<211> LENGTH: 15
<212> TYPE: PRT
<213> ORGANISM: Equus ferus

<400> SEQUENCE: 15

Val Glu Ala Asp Ile Ala Gly His Gly Gln Glu Val Leu Ile Arg
1               5                   10                  15

<210> SEQ ID NO 16
<211> LENGTH: 16
<212> TYPE: PRT
<213> ORGANISM: Equus ferus

<400> SEQUENCE: 16

Tyr Leu Glu Phe Ile Ser Asp Ala Ile Ile His Val Leu His Ser Lys
1               5                   10                  15

<210> SEQ ID NO 17
<211> LENGTH: 6
<212> TYPE: PRT
<213> ORGANISM: Equus ferus

<400> SEQUENCE: 17

Ala Leu Glu Leu Phe Arg
1               5

<210> SEQ ID NO 18
<211> LENGTH: 4
<212> TYPE: PRT
<213> ORGANISM: Equus ferus

<400> SEQUENCE: 18

Glu Leu Phe Arg
1

<210> SEQ ID NO 19
<211> LENGTH: 14
<212> TYPE: PRT
<213> ORGANISM: Equus ferus

<400> SEQUENCE: 19

Thr Gly Gln Ala Pro Gly Phe Thr Tyr Thr Asp Ala Asn Lys
1               5                   10

<210> SEQ ID NO 20
<211> LENGTH: 11
<212> TYPE: PRT
<213> ORGANISM: Equus ferus

<400> SEQUENCE: 20

Thr Gly Pro Asn Leu His Gly Leu Phe Gly Arg
1               5                   10

<210> SEQ ID NO 21
<211> LENGTH: 4
<212> TYPE: PRT
<213> ORGANISM: Equus ferus

<400> SEQUENCE: 21

Thr Gly Pro Asn
1

<210> SEQ ID NO 22
<211> LENGTH: 9
<212> TYPE: PRT
<213> ORGANISM: Equus ferus

<400> SEQUENCE: 22

Thr Gly Pro Asn Leu His Gly Leu Phe
1               5

<210> SEQ ID NO 23
<211> LENGTH: 7
<212> TYPE: PRT
<213> ORGANISM: Equus ferus

<400> SEQUENCE: 23

Met Ile Phe Ala Gly Ile Lys
1               5

<210> SEQ ID NO 24
<211> LENGTH: 8
<212> TYPE: PRT
<213> ORGANISM: Equus ferus

<400> SEQUENCE: 24

Glu Asp Leu Ile Ala Tyr Leu Lys
1               5

```
<210> SEQ ID NO 25
<211> LENGTH: 7
<212> TYPE: PRT
<213> ORGANISM: Equus ferus

<400> SEQUENCE: 25

Lys Tyr Ile Pro Gly Thr Lys
1               5

<210> SEQ ID NO 26
<211> LENGTH: 12
<212> TYPE: PRT
<213> ORGANISM: Equus ferus

<400> SEQUENCE: 26

Glu Glu Thr Leu Met Glu Tyr Leu Glu Asn Pro Lys
1               5                   10

<210> SEQ ID NO 27
<211> LENGTH: 9
<212> TYPE: PRT
<213> ORGANISM: Bos primigenius

<400> SEQUENCE: 27

Thr Leu Ser Asp Tyr Asn Ile Gln Lys
1               5

<210> SEQ ID NO 28
<211> LENGTH: 9
<212> TYPE: PRT
<213> ORGANISM: Bos primigenius

<400> SEQUENCE: 28

Glu Ser Thr Leu His Leu Val Leu Arg
1               5

<210> SEQ ID NO 29
<211> LENGTH: 9
<212> TYPE: PRT
<213> ORGANISM: Bos primigenius

<400> SEQUENCE: 29

Glu Gly Ile Pro Pro Asp Gln Gln Arg
1               5

<210> SEQ ID NO 30
<211> LENGTH: 4
<212> TYPE: PRT
<213> ORGANISM: Bos primigenius

<400> SEQUENCE: 30

Glu Gly Ile Pro
1

<210> SEQ ID NO 31
<211> LENGTH: 13
<212> TYPE: PRT
<213> ORGANISM: Bos primigenius

<400> SEQUENCE: 31

Ile Gln Asp Lys Glu Gly Ile Pro Pro Asp Gln Gln Arg
1               5                   10

<210> SEQ ID NO 32
<211> LENGTH: 6
```

```
<212> TYPE: PRT
<213> ORGANISM: Bos primigenius

<400> SEQUENCE: 32

Met Gln Ile Phe Val Lys
1               5

<210> SEQ ID NO 33
<211> LENGTH: 16
<212> TYPE: PRT
<213> ORGANISM: Bos primigenius

<400> SEQUENCE: 33

Thr Ile Thr Leu Glu Val Glu Pro Ser Asp Thr Ile Glu Asn Val Lys
1               5                   10                  15
```